(12) United States Patent
White et al.

(10) Patent No.: US 7,691,609 B2
(45) Date of Patent: Apr. 6, 2010

(54) MODIFIED XYLANASE EXHIBITING IMPROVED EXPRESSION

(75) Inventors: Theresa C. White, Ottawa (CA); Genevieve R. Giroux, Gloucester (CA); Katie E. A. Wallace, Nepean (CA)

(73) Assignee: Iogen Bio-Products Corporation, Ontario (CA)

( * ) Notice: Subject to any disclaimer, the term of this patent is extended or adjusted under 35 U.S.C. 154(b) by 0 days.

(21) Appl. No.: 12/266,666

(22) Filed: Nov. 7, 2008

(65) Prior Publication Data

US 2009/0111155 A1 Apr. 30, 2009

Related U.S. Application Data

(62) Division of application No. 11/088,725, filed on Mar. 25, 2005, now Pat. No. 7,456,005.

(60) Provisional application No. 60/556,061, filed on Mar. 25, 2004.

(51) Int. Cl.
*C12N 21/06* (2006.01)
*C12N 9/24* (2006.01)
*C12N 19/64* (2006.01)
*C12N 1/00* (2006.01)

(52) U.S. Cl. ............................ 435/69.1; 435/6; 435/200; 435/254.2; 435/91.1; 435/471; 435/476; 435/254.6

(58) Field of Classification Search ....................... None
See application file for complete search history.

(56) References Cited

U.S. PATENT DOCUMENTS

| | | | |
|---|---|---|---|
| 5,405,769 | A | 4/1995 | Campbell et al. |
| 5,759,840 | A | 6/1998 | Sung et al. |
| 5,866,408 | A | 2/1999 | Sung et al. |
| 6,635,464 | B1 | 10/2003 | Paloheimo et al. |
| 6,667,170 | B1 | 12/2003 | Mantylaet et al. |
| 2005/0208178 | A1 | 9/2005 | Bauer et al. |

FOREIGN PATENT DOCUMENTS

| | | |
|---|---|---|
| WO | 94/24270 | 10/1994 |
| WO | 00/29587 | 5/2000 |
| WO | 01/92487 | 12/2001 |
| WO | 02/02597 | 1/2002 |
| WO | 02/36752 | 5/2002 |
| WO | 03/004619 | 6/2003 |
| WO | 03/106484 | 12/2003 |
| WO | 03/106654 | 12/2003 |

OTHER PUBLICATIONS

Hakulinen, et al., "Three-dimensional structures of thermophilic . . . ", Eur. J. Biochem., vol. 270 (2003) 1399-1412.
Sapag, et al., "The endoxylanases from family 11: computer analysis of . . . ", J. Biotech, vol. 95 (2002) 109-31.
Torronen, et al., "Three-dimensional structure of endo-1,4-B-xylanase II from . . . ", The EMBO Journal, vol. 13, No. 11 (1994) 2493-2501.
Arase, et al., "Stabilization of xylanase by random mutagenesis", FEBS Lett., vol. 316, No. 2 (1993) 123-27.
Berges, et al., "Isolation of uridine auxotrophs from *Trichoderma reesei* and efficient transformation with the cloned ura3 and ura5 genes", Curr. Genet., vol. 19 (1991) 359-65.
Berka, et al., "The development of *Aspergillus niger* var. awarmori as a host for the expression and secretion of heterologous gene products", Biochem. Soc. Trans., vol. 19 (1991) 681-85.
Bissett, "A revision of the genus *Trichoderma* I. Section Longibrachiatum sect. nov.,", Can. J. Bot., vol. 62 (1984) 924-31.
Cannon, "International Commission on the Taxomony of Fungi (ICTF): name changes in fungi of microbiological, industrial and medical importance, Part 2", Microbiological Sciences, vol. 3, No. 9 (1986).
Chen, et al., "Nucleotide sequence and deduced primary structure of cellobiohydrolase II from *Trichoderma reesei*", Bio/Technology, vol. 5 (1987) 274-78.
Conesa, et al., "The secretion pathway in filamentous fungi: a biotechnological view", Fung. Genet. Biol., vol. 33 (2001) 155-71.
Goldman, et al., "Transformation of *Trichoderma harzianum* by high-voltage electric pulse", Curr. Genet., vol. 17 (1990) 169-74.
Gritz, et al., "Plasmid-encoded hygromycin B resistance: the sequence of hygromycin B phosphotransferase gene and its expression in *Escherichia coli* and *Saccharomyces cerevisiae*", Gene, vol. 25 (1983) 179-88.
Henrissat, et al., "A classification of glycosyl hydrolases based on amino acid sequence similarities", Biochem., vol. 280 (1991) 309-16.
Hui, et al., "Characterization of cellobiohydrolase I (Cel7A) glycoforms from extracts of *Trichoderma reesei* using capillary isoelectric focusing and electrospray mass spectrometry", J. Chrom. B., vol. 752 (2001) 349-68.
Hui, et al., "Identification of glycan structure and glycosylation sites in cellobiohydrolase II and endoglucanases I and II from *Trichoderma reesei*", Glycobiology, vol. 12, No. 12 (2002) 837-49.
Kuhls, et al., "Molecular evidence that the asexual industrial fungus *Trichoderma reesei* is a clonal derivative of the ascomycete *Hypocrea jecorina*", Proc. Natl. Acad. Sci., vol. 93 (1996) 7755-60.

(Continued)

*Primary Examiner*—Ganapathirama Raghu
*Assistant Examiner*—Md. Younus Meah
(74) *Attorney, Agent, or Firm*—Fitzpatrick, Cella, Harper & Scinto

(57) ABSTRACT

A modified Family 11 xylanase enzyme comprising a sequence that introduces a functional consensus glycosylation site is provided. Non-limiting examples of introduced glycosylation sites include mutation of the amino acid at position 34, 131, 180, 182, or a combination thereof, to an asparagine. The indicated amino acid position in the Family 11 xylanase is determined from sequence alignment of the xylanase of interest with that of a *Trichoderma reesei* xylanase II amino acid sequence. The introduced consensus glycosylation site facilitates increased expression efficiency of the modified xylanase when compared to the expression efficiency of a corresponding xylanase from which the modified xylanase was derived, using similar host strains and growth conditions.

14 Claims, 10 Drawing Sheets

OTHER PUBLICATIONS

Kulkarni, et al., "Molecular and biotechnical aspects of xylanases", FEMS Microbiology Reviews, vol. 23 (1999) 411-56.

Lorito, et al., "Biolistic transformation of *Trichoderma harzianum* and *Gliocladium virens* using plasmid and genomic DNA", Curr. Genet., vol. 24 (1993) 349-56.

Luthi, "Xylanase from the Extremely Thermophilic Bacterium '*Caldocellum saccharolyticum*': Overexpression of the Gene in *Escherichia coli* and Characterization of the Gene Product", Appl. Environ. Microbiol., vol. 56, No. 9 (1990) 2677-83.

Mandels, et al., "Induction of cellulase in *Trichoderma viride* as influenced by carbon sources and metals", J. Bacteriol., vol. 73 (1956) 269-78.

Montenecourt, et al., "Selective Screening Methods for the isolation of high yielding cellulase mutants of *Trichoderma reesei*", Adv. Chem. Ser., vol. 181 (1979) 289-301.

Paloheimo, et al., "High-yield production of a bacterial xylanase in the filamentous fungus *Trichoderma reesei* requires a carrier polypeptide with an intact domain structure", Appl. Environ. Microbiol., vol. 69, No. 12 (2003) 7073-82.

Penttila, et al., "A versatile transformation system for the cellulolytic fungus *Trichoderma reesei*", Gene, vol. 61 (1987) 155-64.

Radford, et al., "Regulation of pyrimidine metabolism in Neurospora", In Molecular Genetics of Filamentous Fungi (1985) 127-43.

Saarelainen, et al., "Cloning, sequencing and enhanced expression of the *Trichoderma reesei* endoxylanase II (pI 9), xln2", Mol. Gen. Genet., vol. 241 (1993) 497-503.

Sagt, et al., "Introduction of an N-glycosylation site increases secretion of heterologous protein in yeasts", Appl. Environ. Microbiol., vol. 66, No. 11 (2000) 4940-44.

Saloheimo, et al., "The protein disulphide isomerase gene of the fungus *Trichoderma reesei* is induced by endoplasmic reticulum stress and regulated by the carbon source", Mol. Gen. Genet., vol. 262 (1999) 35-45.

Shoemaker, et al., "Molecular cloning of exo-cellobiohydrolyase 1 dervied from *Trichoderma reesei* strain L27", Bio/Technology vol. 1 (1983) 691-96.

Simmons, et al., "Classification of Some Cellulase-Producing *Trichoderma* Species", Second International Mycological Congress—Abstracts, vol. M-Z (1977).

Simpson, et al., "An extremely thermostable xylanase from the termophiulic eubacterium Thermotoga", Biochem. J., vol. 277 (1991) 413-17.

Sung, et al., "Overexpression of the *Bacillus subtilis* and circulans Xylanases in *Escherichia coli*", Protein Expression Purif., vol. 4 (1993) 200-06.

Te'o, et al., "Codon optimization of xylanase gene xynB from the thermophilic bacterium *Dictyoglomus thermophilum* for expression in the filamentous fungus *Trichoderma reesei*", FEMS Microbiol. Letters, vol. 190 (2000) 13-9.

Torronen, et al., "The two major xylanases from *Trichoderma reesei*: characterization of both enzymes and genes", Bio/technology, vol. 10 (1992) 1461-65.

Tsai, et al., "Retro-translocation of proteins from the endoplasmic reticulum into the cytosol", Nature Reviews-Molecular Cell biology, vol. 3 (2002) 246-55.

Turunen, et al., "A combination of weakly stabilizing mutations with a disulfide bridge in the alpha-helix region of *Trichoderma reesei* endo-1,4-beta-xylanase II increase the thermal stability through synergism", J. Biotech., vol. 88 (2001) 37-46.

Van Den Elzen, et al., "A chimaeric hygromycin resistance gene as a selectable marker in plant cells", Plant Mol. Biol., vol. 5 (1985) 299-302.

Vanhanen, et al., "Isolation and characterization of the 3-phosphoglycerate kinase gene (pgk) from the filamentous fungus *Trichoderma reesei*", Curr. Genet., vol. 15 (1989) 181-86.

Vanhanen, et al., "Promoter structure and expression of the 3-phosphoglycerate kinase-encoding gene (pgk1) of *Trichoderma reesei*", Gene, vol. 106 (1991) 129-33.

Vieira, et al., "Isolation of single-stranded plasmid DNA", Methods Enzymol., vol. 153 (1987) 3-11.

Winterhalter, et al., "Two extremely thermostable xylanases of the hyperthermophilic bacterium *Thermotoga maritma* MSB8", Appl. Environ. Microbiol., vol. 61, No. 5 (1995) 1810-15.

Davidson, et al., "Incorporation of an Additional Glycosylation Site Enhances Expression of Functional Human Gonadotropin-Releasing Hormone Receptor", Endocrine, vol. 4, No. 3 (1996) 207-12.

Miao, et al., "Bioengineering of coagulation factor VIII for improved secretion", Blood, vol. 103, No. 9 (2004) 3412-19.

```
Ca   23                                                      S AFNTQAAP  31
Cs    1                                                        G          1

Tr2#                   10         20         30         40
                        |          |          |          |
Bp    1  RTITNNEMGN HSGYDYELWK DYGNT-SMTL NNGGAFSAGW N--NIGNA  45
Ca   32  KTITSNEIGV NGGYDYELWK DYGNT-SMTL KNGGAFSCQW S--NIGNA  76
Fs    1  NSSVTGNVG  SSPYHYEIWY QGG-NNSMTF YDNGTYKASW N---GTNDF 44
Cs    2  RIIYDNETGT HGGYDYELWK DYGNT-IMEL NDGGTFSCQW S--NIGNA  46
Rf    1  SAADQQTRGN VGGYDYEMWN QNGQGQASMN PGAGSFTCSW S--NIENF  46
Tr2   1  QTIQPGTGY  NNGYFYSYWN DGHGGVTYTN GPGGQFSVNW S--NSGNF  45
Tv    1  QTIGPGTGF  NNGYFYSYWN DGHGGVTYTN GPGGQFSVNW S--NSGNF  45
Th    1  QTIGPGTGY  SNGYYYSYWN DGHAGVTYTN GGGGSFTVNW S--NSGNF  45
Sc    1  SGTPSSTGT  DGGYYYSWWT DGAGDATYQN NGGGSYTLTW SG-NNGNL  46
An    1         S   AGINYVQNYN GNLGDFTY-D ESAGTFSMYW EDGVSSDF  38
Ak    1         S   AGINYVQNYN GNLADFTY-D ESAGTFSMYW EDGVSSDF  38
At    1         S   AGINYVQNYN GNLGDFTY-D ESAGTFSMYW EDGVSSDF  38
Tr1   1             ASINYDQNYQ TGG-QVSYS- PSNTGFSVNW N--TQDDF  34
Aa    1  RSTPSSTGE  NNGYYYSFWT DGGGDVTYTN GNAGSYSVEW S--NVGNF  45
Ss    1  ATTIT-NETGY D-GMYYSFWT DGGGSVSMTL NGGGSYSTRW T--NCGNF  45
S1B   1  DTVVTTNQEGT NNGYYYSFWT DSQGTVSMNM GSGGQYSTSW R--NTGNF  47
S1C   1  ATTITTNQTGT D-GMYYSFWT DGGGSVSMTL NGGGSYSTQW T--NCGNF  46
T1    1  QTTPNSEGW  HDGYYYSWWS DGGAQATYTN LEGGTYEISW G---DGGNL 45
Tf    1  AVTSNETGY  HDGYFYSFWT DAPGTVSMEL GPGGNYSTSW R--NTGNF  45
Bc    1             ASTDYWQNWT DGGGIVNAVN GSGGNYSVNW S--NTGNF  36
Bs    1             ASTDYWQNWT DGGGIVNAVN GSGGNYSVNW S--NTGNF  36
```

FIGURE 1

```
Tr2#              50              60              70   *       80
                  |               |               |            |
Bp    46  LFRK-GKKFD ST-RTHHQLG NISINYNASF N-PGGNSYLC VYGWTQSP   90
Ca    77  LFRK-GKKFN DT-QTYKQLG NISVNYNCNY Q-PYGNSYLC VYGWTSSP  121
FS    45  LARV-GFKYD EK-HTYEELGPIDAYYKWSKQ GSAGGYNYIG IYGWTVDP   91
Cs    47  LFRK-GRKFN SD-KTYQELG DIVVEYGCDY N-PNGNSYLC VYGWTRNP   91
Rf    47  LARM-GKNYD SQKKNYKAFG NIVLTYDVEY T-PRGNSYMC VYGWTRNP   92
Tr2   46  VGGK-GWQPG TKNKV----- ---INFS-GS YNPNGNSYLS VYGWSRNP   83
Tv    46  VGGK-GWQPG TKNKV----- ---INFS-GT YNPNGNSYLS VYGWSRNP   83
Th    46  VGGK-GWQPG TKNKV----- ---INFS-GS YNPNGNSYLS IYGWSRNP   83
Sc    47  VGGK-GWNPG AASRS----- ---ISYS-GT YQPNGNSYLS VYGWTRSS   84
An    39  VVGL-GWTTG SSNA------ ---ITYSAEY SASGSSSYLA VYGWVNYP   77
Ak    39  VVGL-GWTTG SSNA------ ---ISYSAEY SASGSSSYLA VYGWVNYP   77
At    39  VVGL-GWTTG SSNA------ ---ITYSAEY SASGSASYLA VYGWVNYP   77
Tr1   35  VVGV-GWTTG SSAP------ ---INFGGSF SVNSGTGLLS VYGWSTNP   72
Aa    46  VGGK-GWNPG SAKD------ ---ITYSGNF T-PSGNGYLS VYGWTTDP   83
Ss    46  VAGK-GWANG GR-RT----- ---VRYT-GW FNPSGNGYGC LYGWTSNP   82
SlB   48  VAGK-GWANG GR-RT----- ---VQYS-GS FNPSGNAYLA LYGWTSNP   84
SlC   47  VAGK-GWSTG DGN------- ---VRYN-GY FNPVGNGYGC LYGWTSNP   82
Tl    46  VGGK-GWNPG LNARA----- ---IHFE-GV YQPNGNSYLA VYGWTRNP   83
Tf    46  VAGK-GWATG GR-RT----- ---VTYS-AS FNPSGNAYLT LYGWTRNP   82
Bc    37  VVGK-GWTTG SPFRT----- ---INYNAGV WAPNGNGYLT LYGWTRSP   75
Bs    37  VVGK-GWTTG SPFRT----- ---INYNAGV WAPNGNGYLT LYGWTRSP   75

Tr2#              90             100             110            120            130
                  |               |          *     |              |              |
Bp    91  LAEYYIVDSW GTYR-PT--G AYKGSFYADG GTYDIYETTR VNQPSIIG  135
Ca   122  LVEYYIVDSW GSWRPP--GG TSKGTITVDG GIYDIYETTR INQPSIQG  167
Fs    92  LVEYYIVDDW FNKPGANLLG QRKGEFTVDG DTYEIWQNTR VQQPSIKG  139
Cs    92  LVEYYIVESW GSWRPP--GA TPKGTITQWMAGTYEIYETTR VNQPSIDG  138
Rf    93  LMEYYIVEGW GDWRPPGNDG EVKGTVSANG NTYDIRKTMR YNQPSLDG  140
Tr2   84  LIEYYIVENF GTYN-PSTGA TKLGEVTSDG SVYDIYRTQR VNQPSIIG  130
Tv    84  LIEYYIVENF GTYN-PSTGA TKLGEVTSDG SVYDIYRTQR VNQPSIIG  130
Th    84  LIEYYIVENF GTYN-PSTGA TKLGEVTSDG SVYDIYRTQR VNQPSIIG  130
Sc    85  LIEYYIVESY GSYD-PSSAA SHKGSVTCNG ATYDILSTWR YNAPSIDG  131
An    78  GAEYYIVEDY GDYN-PCSSA TSLGTVYSDG STYQVCTDTR INEPSITG  124
Ak    78  QAEYYIVEDY GDYN-PCSSA TSLGTVYSDG STYQVCTDTR TNEPSITG  124
At    78  QAEYYIVEDY GDYN-PCSSA TSLGTVYSDG STYQVCTDTR TNEPSITG  124
Tr1   73  LVEYYIMEDN HNY--PAQ-G TVKGTVTSDG ATYTIWENTR VNEPSIQG  117
Aa    84  LIEYYIVESY GDYN-PGSGG TTRGNVSSDG SVYDIYTATR TNAPSIQG  130
Ss    83  LVEYYIVDNW GSYR-PT--G ETRGTVHSDG GTYDIYKTTR YNAPSVEA  127
SlB   85  LVEYYIVDNW GTYR-PT--G EYKGTVTSDG GTYDIYKTTR VNKPSVEG  129
SlC   83  LVEYYIVDNW GSYR-PT--G TYKGTVSSDG GTYDIYQTTR YNAPSVEG  127
Tl    84  LVEYYIVENF GTYD-PSSGA TDLGTVECDG SIYRLGKTTR VNAPSIDG  130
Tf    83  LVEYYIVESW GTYR-PT--G TYMGTVTTDG GTYDIYKTTR YNAPSIEG  127
Bc    76  LIEYYVVDSW GTYR-PT--G TYKGTVKSDG GTYDIYTTTR YNAPSIDG  120
Bs    76  LIEYYVVDSW GTYR-PT--G TYKGTVKSDG GTYDIYTTTR YNAPSIDG  120
```

FIGURE 1 CONT'D

```
Tr2#                            140             150        160
                                 |               |          |
Bp  136   -IATFKQYWS  VRQTKRTS--  ------GTVS  VSAHFRKWES  LGMPM-GK  174
Ca  168   -NTTFKQYWS  VRRTKRTS--  ------GTIS  VSKHFAAWES  KGMPL-GK  206
Fs  140   -TQTFPQYFS  VRKSARSC--  ------GHID  ITAHMKKWEE  LGMKM-GK  178
Cs  139   -TATFQQYWS  VRTSKRTS--  ------GTIS  VTEHFKQWER  MGMRM-GK  177
Rf  141   -TATFPQYWS  VRQTSGSANN  QTNYMKGTID  VTKHFDAWSA  AGLDMSGT  187
Tr2 131   -TATFYQYWS  VRRNHR-S-S  ------GSVN  TANHFNAWAQ  QGLTL-GT  168
Tv  131   -TSTFYQYWS  VRRTHR-S-S  ------GSVN  TANHFNAWAQ  QGLTL-GT  168
Th  131   -TATFYQYWS  VRRNHR-S-S  ------GSVN  TANHFNAWAS  HGLTL-GT  168
Sc  132   -TQTFEQFWS  VRNPKKAPGG  SIS---GTVD  VQCHFDAWKG  LGMNLGSE  175
An  125   -TSTFTQYFS  VRESTRTS--  ------GTVT  VANHFNFWAQ  HGFGN-SD  163
Ak  125   -TSTFTQYFS  VRESTRTS--  ------GTVT  VANHFNFWAQ  HGFGN-SD  163
At  125   -TSTFTQYFS  VRESTRTS--  ------GTVT  VANHFNFWAH  HGFGN-SD  163
Tr1 118   -TATFNQYIS  VRNSPR-T-S  ------GTVT  VQNHFNAWAS  LGLHLGQM  155
Aa  131   -TATFSQYWS  VRQNKR-VG-  ------GTVT  TSNHFNAWAK  LGMNL-GT  168
Ss  128   -PAAFDQYWS  VRQSKVT--S  ------GTIT  TGNHFDAWAR  AGMNMGNF  168
SlB 130   TR-TFDQYWS  VRQSKR-TG-  ------GTIT  TGNHFDAWAR  AGMPLGNF  168
SlC 128   TK-TFQQYWS  VRQSKVTSGS  ------GTIT  TGNHFDAWAR  AGMNMGQF  168
Tl  131   TQ-TFDQYWS  VRQDKR-T-S  ------GTVQ  TGCHFDAWAR  AGLNVNGD  169
Tf  128   TR-TFDQYWS  VRQSKRTS--  ------GTIT  AGNHFDAWAR  HGMHLGTH  166
Bc  121   DRTTFTQYWS  VRQSKRPTGS  N-----ATIT  FTNHVNAWKS  HGMNLGSN  163
Bs  121   DRTTFTQYWS  VRQSKRPTGS  N-----ATIT  FSNHVNAWKS  HGMNLGSN  163

Tr2#         170         180         190
              |           |           |
Bp  175   MYETAFTVEG  YQSSGSANVM  TNQLFIGN         201
Ca  207   MHETAFNIEG  YQSSGKADVN  SMSINIGK         233
Fs  179   MYEAKVLVEA  GGGSGSFDV-  TYFKMT           203
Cs  178   MYEVALTVEG  YQSSGYANVY  KNEIRIGANP....
Rf  188   LYEVSLNIEG  YRSNGSANVK  SVSV             211
Tr2 169   MDYQIVAVEG  YFSSGSASI-  TVS              190
Tv  169   MDYQIVAVEG  YFSSGSASI-  TVS              190
Th  169   MDYQIVAVEG  YFSSGSASI-  TVS              190
Sc  176   HNYQIVATEG  YQSSGTATI-  TVT              197
An  164   FNYQVMAVEA  WSGAGSASV-  TISS             184
Ak  164   FNYQVMAVEA  WSGAGSASV-  TISS             184
At  164   FNYQVVAVEA  WSGAGSASV-  TISS             184
Tr1 157   -NYQVVAVEG  WGGSGSASQ-  SVSN             178
Aa  169   HNYQILATEG  YQSSGSSSI-  TIQ              190
Ss  167   RYYMINATEG  YQSSGSSTI-  TVSG             189
SlB 169   SYYMIMATEG  YQSSGSSSI-  NVGG........
SlC 169   RYYMIMATEG  YQSSGSSNI-  TVSG             191
Tl  170   HYYQIVATEG  YFSSGYARI-  TVADVG           194
Tf  167   D-YMIMATEG  YQSSGSSNVT  LGTS........
Bc  164   WAYQVMATEG  YQSSGSSNV-  TVW              185
Bs  164   WAYQVMATEG  YQSSGSSNV-  TVW              185
```

FIGURE 1 CONT'D

MODIFIED XYLANASE EXHIBITING IMPROVED EXPRESSION

This application is a division of application Ser. No. 11/088,725 filed Mar. 25, 2005, which in turn is nonprovisional of application No. 60/556,061 filed Mar. 25, 2004.

The present invention relates to xylanases with improved expression, more particularly to the improved expression and secretion of xylanases from a host.

BACKGROUND OF THE INVENTION

Xylanases, produced by many species of filamentous fungi and bacteria, are a group of enzymes with wide commercial utility. A major application of xylanases is for biobleaching pulp in the production of paper. In addition, xylanases have been used as clarifying agents in juices and wines, as enzymatic agents in the washing of precision devices and semiconductors and they are also used for improving digestibility of poultry and swine feed.

Most xylanases exploited for industrial applications are members of Family 11, showing diversity in their biochemical and biophysical properties. For example, thermostable xylanases have been isolated from bacteria (U.S. Pat. No. 6,667,170), fungi (U.S. Pat. No. 6,635,464), or other extreme thermophiles (Lüthi et al. 1990; Winterhalter et al. 1995; Simpson et al. 1991). Alternatively, xylanase performance has been optimised for various industrial applications via protein engineering (e.g. U.S. Pat. No. 5,759,840; U.S. Pat. No. 5,866,408; U.S. Pat. No. 5,405,769; and Turunen et al., 2001).

Successful implementation of xylanase enzymes in industrial applications requires economical production from a host microbe, which secretes the xylanase into the culture broth during submerged fermentation. This is particularly necessary for the large-scale production of xylanases from thermophiles or extreme thermophiles that are difficult to culture or do not secrete sufficiently high levels of protein. Typically, the host microbe for the production of industrial enzymes is a filamentous fungus such as *Trichoderma, Aspergillus* or *Fusarium*, an actinomycete such as *Streptomyces* or a species of *Bacillus* bacteria. This means that the genes encoding a target xylanase, whether isolated from a different organism or from protein engineering of a xylanase gene from the host organism, must be cloned into the production host in such a way that the gene is operably linked to the DNA sequences that will facilitate its expression and secretion from the host.

Expression and secretion of exogenous proteins by genetic modification of industrial strains of *T. reesei* has remained a significant challenge for many years (Conesa et al., 2001). Expression of heterologous proteins in *T. reesei* elicits an Unfolded Protein Response (UPR; Saloheimo et al., 1999), which results from an accumulation of unfolded or misfolded nascent polypeptides in the lumen of the endoplasmic reticulum (ER). Because of the limited information currently available on the mechanisms regulating folding and secretion of the Family 11 xylanases from *T. reesei*, several strategies have been implemented to facilitate high-level expression of related exogenous xylanases in *T. reesei* host strains. These include the use of highly inducible promoters, such as those of the *T. reesei* cellulase genes, and replacement of the native cellulase genes with xylanase expression constructs containing highly inducible promoters.

Expression of bacterial xylanases from *T. reesei* may require fusion of the xylanase to a carrier *T. reesei* polypeptide with an intact domain structure, such as the catalytic core or binding domains of the *T. reesei* mannanase I or CBH II proteins (Paloheimo, et al., 2003). This strategy, alone or in combination with deletion of one or more cellulase gene(s) from the host *T. reesei* strain, was disclosed in U.S. Pat. No. 6,635,464 and U.S. Pat. No. 6,667,170 to direct the expression thermophilic Family 11 xylanases from both bacterial (*A. flexuosa*) and fungal (*C. thermophilus*) sources. Although the carrier polypeptide certainly increased the production and secretion of the heterologous xylanases disclosed in U.S. Pat. No. 6,635,464 and U.S. Pat. No. 6,667,170 from *T. reesei* host strains, it is not always desirable to have a carrier polypeptide attached to the xylanase enzyme for industrial applications. In these cases, the carrier polypeptide would need to be removed by proteolysis subsequent to secretion of the fusion protein into the culture broth and prior to its use in the application. However proteolysis adds both time and cost to the overall production of the target xylanase due to cost and incubation time required for the proteolysis step itself as well as potential yield losses of the target xylanase during the proteolytic removal of the carrier polypeptide.

This strategy of using a fusion of a target protein to a carrier protein native to the host cell has also been employed successfully to increase the production and secretion of mammalian chymosin from *Aspergillus* (Van den Brink et al., WO 02/36752 and WO 03/106484). WO 03/106484 discloses further improvements in the production and secretion of glucoamylase-chymosin fusion proteins from *Aspergillus* by the introduction of an N-glycosylation motif within the artificial linker polypeptide between the chymosin and glucoamylase fusion partners or within the chymosin peptide sequence. However, there was no demonstration of the benefits of chymosin production from *Aspergillus* via the introduction of a glycosylation motif in a construct not containing a fusion partner.

Sagt et al. (2000) report improvements in secretion of a target protein from a heterologous eukaryotic host via introduction of an N-glycosylation motif within the target protein. In this report, introduction of an N-glycosylation site into the sequence of a hydrophobic mutant of either a fungal cutinase or of native llama antibody fragments resulted in increased secretion of the target protein from *Saccharomyces* of *Pichia* yeast host. However, introduction of the glycosylation site into the native fungal cutinase did not result in any increase in expression from the heterologous yeast hosts.

WO 02/02597 reports the production of the FSH-alpha subunit and glucocerebrosidase polypeptides containing a glycosylation site. The goal of these studies was to improve the stability and expression of these polypeptides. However, the applicability of the method was only demonstrated using the addition of short nucleotide sequences encoding the N-glycosylation motif rather than via direct modification of the primary peptide sequence.

It is an object of the present invention to provide modified xylanases exhibiting improved expression.

SUMMARY OF THE INVENTION

The present invention relates to xylanases with improved expression, more particularly to the improved expression and secretion of xylanases from a host.

The present invention provides a modified Family 11 xylanase comprising, a sequence that introduces a functional consensus N-glycosylation site that is otherwise not found in the Family 11 xylanase from which the modified Family 11 xylanase is derived. The modified Family 11 xylanase may comprise a substitution of an amino acid at a position selected from the group consisting of position 34 (X34N), position 131 (X131N), position 180 (X180N), position 182 (X182N), and a combination thereof, to an asparagine, the position determined from sequence alignment of the Family 11 xylanase with the amino acid sequence of *Trichoderma reesei* xylanase II as defined in SEQ ID NO:1. The present invention also pertains to a modified Family 11 xylanase as described above, and further comprising, a substitution of an amino acid at a position selected from the group consisting of position 36 (X34N-S36T), position 182 (X180N-S182T), position 184 (X182N-S184T), and a combination thereof, to a threonine. Preferably, the modified Family 11 xylanase comprises a X131N mutation. Also provided is a modified Family 11 xylanase selected from the group consisting of: ITX1, ITX2, ITX3, ITX3', ITX4, ITX4', ITX5, ITX5', Xln1-131N, and *S. lividans* xlnC-131N.

The present invention is directed to a modified Family 11 xylanase as described above, wherein the modified xylanase when expressed in a *Trichoderma* host strain exhibits an increase in expression efficiency of at least 40% when compared to the expression efficiency of a Family 11 xylanase from which the modified xylanase is derived.

The present invention also provides a modified Family 11 xylanase genetic construct comprising a promoter operatively linked to a secretion signal that is operatively linked to a coding region, the coding region comprising a functional consensus N-glycosylation site that is otherwise not found in the Family 11 xylanase from which the modified Family 11 xylanase is derived, the modified xylanase genetic construct resulting in an increase in expression efficiency of an encoded modified xylanase when compared to the expression efficiency of an encoded Family 11 xylanase from which the encoded modified xylanase was derived.

Furthermore, there is provided a genetically modified microbe comprising the modified Family 11 xylanase genetic construct as just described. Preferably, the genetically modified microbe comprises a member of the genus of *Trichoderma* or *Hypocrea*. Furthermore, the genetically modified microbe comprises a secretion signal that is a *Trichoderma* secretion signal, for example a *Trichoderma* xylanase secretion signal.

The present invention also pertains to a genetically modified microbe comprising a coding region that encodes a modified xylanase selected from the group consisting of: ITX1, ITX2, ITX3, ITX3', ITX4, ITX4', ITX5, ITX5', Xln1-131N, and *S. lividans* xlnC-131N.

The present invention provides a method of processing food or feed comprising, treating the food or feed with an additive comprising the modified Family 11 xylanase comprising, a sequence that introduces a functional consensus N-glycosylation site that is otherwise not found in the Family 11 xylanase from which the modified Family 11 xylanase is derived. For example the food or feed additive may be selected from the group consisting of a poultry feed additive, a swine feed additive, a food additive used in baking, or a food additive used in brewing.

The present invention also pertains to a method of paper pulp manufacturing comprising treating the pulp with a modified family 11 xylanase comprising, a sequence that introduces a functional consensus N-glycosylation site that is otherwise not found in the Family 11 xylanase from which the modified Family 11 xylanase is derived.

The present invention pertains to a use of a modified xylanase comprising, a sequence that introduces a functional consensus N-glycosylation site that is otherwise not found in the Family 11 xylanase from which the modified Family 11 xylanase is derived, in an industrial or food or feed process. The industrial process may be paper pulp manufacturing.

The present invention provides for modified Family 11 xylanases with improved expression and secretion from a *Trichoderma* host without any apparent change in the biochemical properties of the enzyme. The resulting increase in the specific xylanase production and overall protein productivity of the strain facilitates the economical manufacturing of Family 11 xylanase products for industrial applications. Furthermore, in embodiments of the invention, N-glycosylation sites may be introduced into regions of conserved sequence homology at the beginning, middle or end of the Family 11 peptide sequence. This is achieved without any adverse effects on the function of the xylanase.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows the alignment of the amino acid sequences of Family 111 xylanases with numbering from N-terminus, where Bp—*Bacillus pumilus* (SEQ ID NO:31); Ca—*Clostridium acetobutylicum* P262 xynB (SEQ ID NO:33); Cs—*Clostridium stercorarium* xynA (SEQ ID NO:34); Rf—*Ruminococcus flavefaciens* (SEQ ID NO:35); Tr2—*Trichoderma reesei* xyn2 (SEQ ID NO:1); Tv—*Trichoderma viride* (SEQ ID NO:42); Th—*Trichoderma harzianum* (SEQ ID NO:41); Sc—*Schizophyllum commune* xynA (SEQ ID NO:36); An—*Aspergillus niger*, var. *awamori* (SEQ ID NO:43); Ak—*Aspergillus kawachii* XynC (SEQ ID NO:44); At—*Aspergillus tubigensis* (SEQ ID NO:29); Tr1—*Trichoderma reesei* xyn1 (SEQ ID NO:2); Aa—*Aspergillus awamorivar.kawachi* Xyn B (SEQ ID NO:28); Fs—*Fibrobacter succinogenes* Xyn II (SEQ ID NO:45); Ss—*Streptomyces* sp. 36a (SEQ ID NO:37); SlB—*Streptomyces lividans* xynB (SEQ ID NO:38); SlC—*Streptomyces lividans* xynC (SEQ ID NO:39); Tl—*Thermomyces lanuginosus* Xyn (SEQ ID NO:45); Tf—*Thermomonospora fusca* TfxA (SEQ ID NO:40); Bc—*Bacillus circulans* (SEQ ID NO:30); Bs—*Bacillus subtilis* (SEQ ID NO:32);

FIG. 5 shows maps of the vectors used to direct the expression of native (and modified) *T. reesei* xylanase I and *S. lividans* xylanase C, respectively, in *T. reesei*.

DESCRIPTION OF PREFERRED EMBODIMENT

Figure 2:
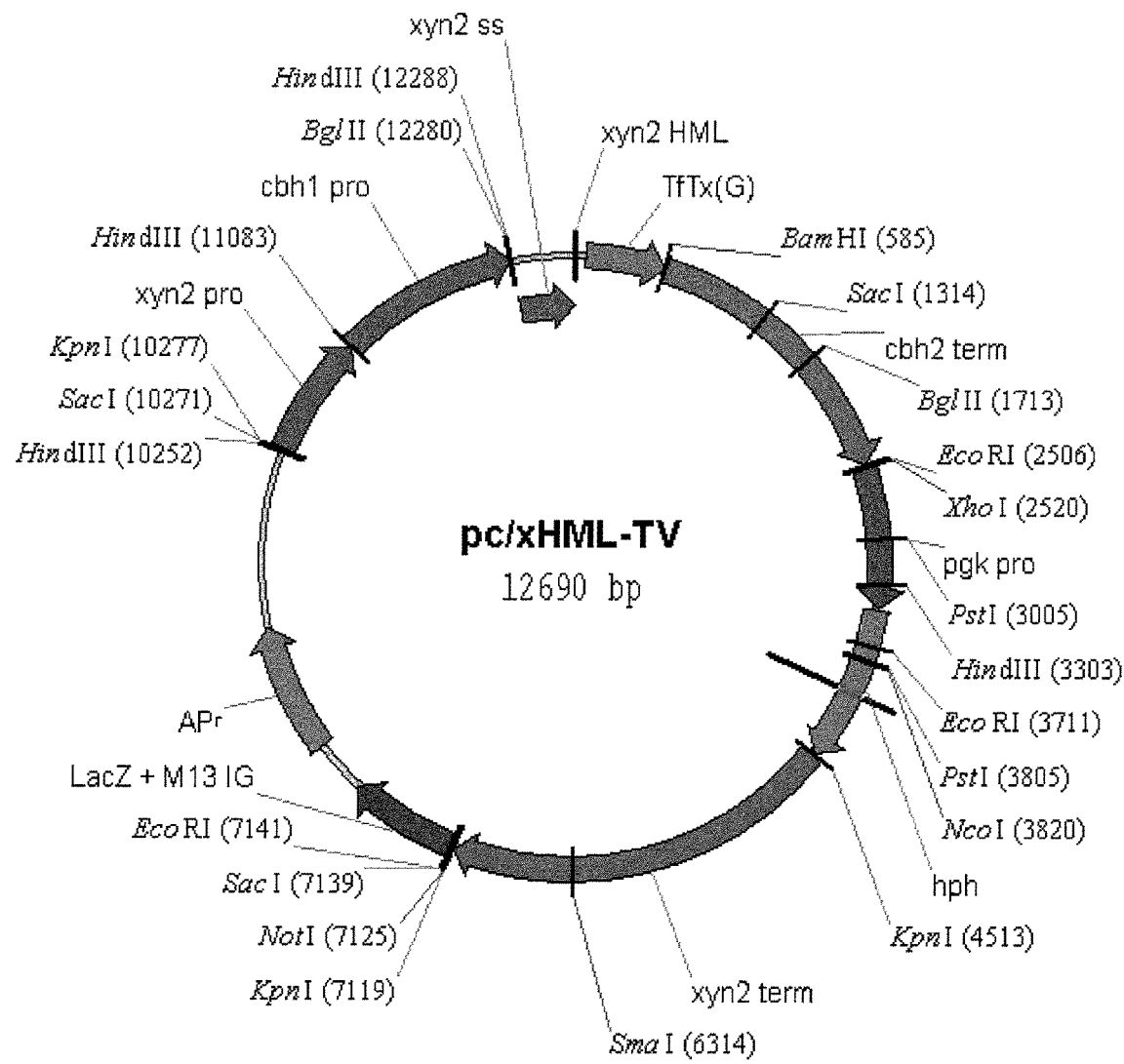
FIG. 2 shows a map of the vector pC/XHML-TV used to direct the expression of a modified xylanase in *T. reesei*.

The present invention relates to xylanases with improved expression, more particularly to the improved expression and secretion of xylanases from a host.

The following description is of a preferred embodiment. Xylanases and modified xylanases, as outlined herein, may be used for the purposes of bleaching paper pulp or other applications requiring activities typically at temperatures and pH above that of the wild-type enzyme. For the biobleaching of pulp, the preferred xylanase is derived from a xylanase classified in Family 11 (see Table 1).

Xylanases are produced by many species of filamentous fungi and bacteria, and can be classified into two families, Family 10 or 11, based primarily on structural and mechanistic similarities (Henrissat, 1991). Family 11 xylanase enzymes are a group of small enzymes of relatively low molecular mass (approximately 20 kDa, and about 200 amino acid residues).

The Family 11 xylanases secreted by *T. reesei* are not glycosylated, which is consistent with the absence of a consensus N-glycosylation motif in the amino acid sequence of xylanase I (Törrönen et al., 1992) However, xylanase II is also not glycosylated, despite the presence of two N-glycosylation consensus motifs in its sequence. In contrast, *T. reesei* cellulases are N-glycosylated at asparagine residues within the consensus motif Asn-Xaa-Ser/Thr, where Xaa is any amino acid other than proline (or N-X-S/T, where X is any amino acid other than proline). However, not all of the potential sites within the various cellulase enzymes are glycosylated (Hui et al., 2001 and 2002). This suggests that the *Trichoderma* organism does not recognize some consensus motifs in native amino acid sequences.

The present invention provides a modified Family 11 xylanase comprising a glycosylation sequence or motif, for example, but not limited to Asn-Xaa-Ser/Thr, Asn-Xaa-Thr, or Asn-Xaa-Ser, that is otherwise not present in the corresponding xylanase from which the modified xylanase is prepared or derived.

Furthermore, the present invention provides a modified Family 11 xylanase having one or more than one amino acid selected from positions 34, 131, 180 and 182 substituted to an asparagine (Asn or N) wherein the position is determined from sequence alignment of the Family 11 xylanase with *Trichoderma reesei* xylanase II amino acid sequence defined in SEQ ID NO:1. Such a substitution may be described as: X34N, X131N, X180N or X182N, where the amino acid "X" is substituted by asparagine or "N" at the indicated position. For example in X131N, indicates that the amino acid "X" at position 131 (as determined from sequence alignment of the Family 11 xylanase with *Trichoderma reesei* xylanase II (TrX II) amino acid sequence defined in SEQ ID NO:1) is substituted by asparagine or "N". Preferably, the mutation is at position 131, producing X131N, or its corresponding position in another Family 11 xylanase as determined by sequence alignment with TrX II (SEQ ID NO:1). It has been observed that the modified xylanase comprising one or more than one of these mutations, for example, the X131N substitution, exhibits an improved expression efficiency compared to the Family 11 xylanase from which the modified xylanase was produced or derived. Examples of constructs comprising the X34N, X131N, X180N or X182N mutations include ITX5 and ITX5', ITX1 and ITX2, ITX3 and ITX3', and ITX4 and ITX4', respectively.

Additional mutations for example, X34N-S36T, X180N-S182T, and X182N-S184T may also be introduced into the Family 11 xylanase to produce the consensus sequence Asn-Xaa-Thr, thereby ensuring that a Thr is positioned upstream from the Asn within the xylanase. Examples of constructs comprising the X34N, S36T; X180N, S182T; or X182N, S184T mutations include ITX5', ITX3', and ITX4', respectively.

The modified xylanase of the present invention may be derived from any Family 11 xylanase, for example a xylanase that is native to *Trichoderma*, including but not limited to *T. reesei* xylanase II, *T. reesei* xylanase I, *Trichoderma viride* xylanase, or a xylanase from *Aspergillus*, *Fusarium*, an actinomycete such as *Streptomyces* for example, but not limited to, *Streptomyces lividans* xylanase B and *Streptomyces lividans* xylanase C, or a xylanase from *Bacillus*, *Thermobifida*, *Actinamadura*, *Chaetomium*, or *Thermatoga*.

Modification of *T. ressei* xylanase I (TrX I) to introduce an equivalent mutation at position 131, as determined by comparison with the sequence of *T. ressei* xylanase II (TrX-II; SEQ ID NO:1), requires a mutation at position 118 of TrX-I (i.e. the mutation T118N). In this case *T. ressei* xylanase I, with a substitution at T118N, comprises an equivalent mutation to that of X131N as found in TrX II (see FIG. 1 for alignments of "Tr1" and "Tr2"). Similarly, modification of *S. lividans* xylanase C, to introduce an equivalent mutation to that at position 131, as determined by comparison with the sequence of TrX-II, requires a mutation at position 128 of *S. lividans* xylanase C (i.e. the mutation T128N). In this case xylanase T128N in *S. lividans* xylanase C comprises an equivalent mutation to that of X131N in TrX-II (see FIG. 1 for alignments of "SlC" and "Tr2").

By the term "xylanase", it is meant an enzyme that hydrolyzes xylan to xylose. Xylanases may possess varying properties, including structure (molecular weight, three-dimensional orientation, amino acid composition, and active site) and catalytic activity (rate and kinetics of xylan hydrolysis, and ability to act on other substrates) as is known to one of skill in the art.

The modified xylanase of the present invention may be derived from a native, or wild-type xylanase, or it may be derived from an already altered xylanase that has been mutagenized and selected or genetically engineered using standard protocols as would be known to one of skill in the art, for example site directed mutagenesis, chemical mutagenesis, or equivalent methods, to alter its pH profile, temperature profile, substrate specificity, or a combination thereof. Examples of such altered xylanases include those disclosed herein, for example but not limited to HTX18 and HTX18-R135Y. Additional examples of altered, or genetically engineered, xylanases that may also be further modified as described herein, include those that are known to one of skill in the art, for example but not limited to those disclosed in WO 00/29587, WO 01/92487 and WO 03/046169 (which are incorporated herein by reference), and include, but are not limited to, TrX-DS1; TrX-162H-DS1; TrX-162H-DS2; TrX-162H-DS4; TrX-162H-DS8; TrX-75A; TrX-HML-105H; TrX-HML-75A-105H; TrX-HML-75C-105R; TrX-HML-75G-105R; TrX-HML-75G-105R-125A-129E; TrX-HML-75G-105H-125A-129E; TrX-HML-75A-105H-125A-129E; TrX-HML-75A-105R-125A-129E; TrX-157D-161R-162H-165H; TrX-HML-AHAE; TrX-HML-AHAE-R; TrX-HML-AHAE-RR; TrX-HML-AHAE-RRR; TrX-HML-AHA-RR-DRHH; TrX-HML-AHAE-RR-DRHH; TrX-HML-AHAE-RRR-DRHH; TrX-116G; TrX-118C; TrX-HML-AHCAE-R; TrX-H-11D-ML-AHGAE-RR; TrX-HML-AHGAE-R; TrX-H-11D-ML-AHGCAE-RR; TrX-H-11D-ML-AHCAE-RR.

A native xylanase or wild-type xylanase is a xylanase that has not been modified or altered outside of the regular course of nature. A native xylanase may comprise mutations that occur naturally.

By "*Trichoderma reesei* xylanase II sequence alignment" or "TrX numbering" it is meant the numbering associated with the position of amino acids based on the amino acid sequence of *Trichoderma reesei* xylanase II (also referred to as TrX II; see Table 1, Tr2; FIG. 1; and SEQ ID NO:1). TrX II is a member of the Family 11 xylanases. Family 11 xylanases exhibit a substantial degree of sequence similarity (see FIG. 1), therefore, by aligning the amino acids to optimize the sequence similarity between xylanase enzymes and by using the amino acid numbering of TrX II (*Trichoderma reesei* xylanase II) as the basis for numbering, the positions of amino acids within other xylanase enzymes can be determined relative to TrX II.

Structural studies indicate that Family 11 xylanases from bacterial and fungal origins share the same general molecular structure (e.g. U.S. Pat. No. 5,405,769), exhibiting three types of secondary structure: beta-sheets, turns and a single alpha helix. A xylanase can be classified as a "Family 11 xylanase" if it comprises similarity to other Family 11 xylanases, in particular two glutamic acid residues at positions 86 and 177 (based on *Trichoderma reesei* xylanase II (TrX II) amino acid numbering) that may serve as catalytic residues. Family 11 xylanases may include those listed in Table 1. Preferably, the xylanase is a *Trichoderma reesei* xylanase II, *Trichoderma reesei* xylanase I, *Trichoderma viride* xylanase, *Streptomyces lividans* xylanase B, *Streptomyces lividans* xylanase C, or a xylanase from *Aspergillus, Fusarium,* or *Bacillus*.

TABLE 1

Representative Family 11 xylanase enzymes from bacteria and fungi.

| Microbe | Xylanase | SEQ ID NO: | Swiss Prot No |
|---|---|---|---|
| *Aspergillus niger* | Xyn A | SEQ ID NO: 43 | — |
| *Aspergillus awamori* var. kawachi | Xyn B | SEQ ID NO: 28 | P48824 |
| *Aspergillus kawachii* | Xyn C | SEQ ID NO: 44 | — |
| *Aspergillus tubigensis* | Xyn A | SEQ ID NO: 29 | — |
| *Bacillus circulans* | Xyn A | SEQ ID NO: 30 | P09850 |
| *Bacillus pumilus* | Xyn A | SEQ ID NO: 31 | P00694 |
| *Bacillus subtilis* | Xyn A | SEQ ID NO: 32 | P18429 |
| *Cellulomonas fimi* | Xyn D | — | P54865 |
| *Chainia* spp | Xyn | — | — |
| *Clostridium acetobutylicum* | Xyn B | SEQ ID NO: 33 | — |
| *Clostridium stercorarium* | Xyn A | SEQ ID NO: 34 | P33558 |
| *Fibrobacter succinognes* | Xyn II | SEQ ID NO: 45 | — |
| *Neocallimasterix patriciarum* | Xyn A | — | P29127 |
| *Nocardiopsis dassonvillei* | Xyn II | — | — |
| *Ruminococcus flavefaciens* | Xyn A | SEQ ID NO: 35 | P29126 |
| *Schizophyllum commune* | Xyn A | SEQ ID NO: 36 | P35809 |
| *Streptomyces* sp. No. 36a | Xyn | SEQ ID NO: 37 | |
| *Streptomyces lividans* | Xyn B | SEQ ID NO: 38 | P26515 |
| *Streptomyces lividans* | Xyn C | SEQ ID NO: 39 | P26220 |
| *Streptomyces thermoviolaceus* | Xyn II | — | — |
| *Thermomonospora fusca* | Xyn A | SEQ ID NO: 40 | — |
| *Thermomyces lanuginosus* | Xyn A | SEQ ID NO: 46 | O43907 |
| *Trichoderma harzianum* | Xyn | SEQ ID NO: 41 | P48793 |
| *Trichoderma reesei* | Xyn I | SEQ ID NO: 2 | P36218 |
| *Trichoderma reesei* | Xyn II | SEQ ID NO: 1 | P36217 |
| *Trichoderma viride* | Xyn | SEQ ID NO: 42 | — |

A modified xylanase of the present invention is any xylanase that is engineered to introduce or comprise a changed glycosylation site when compared to the xylanase from which the modified xylanase was prepared or derived.

Non-limiting examples of such modifications include X34N, X34N-S36T, X131N, X180N, X180N-S182T, X182N, or X182N-S184T (TrX numbering), or a combination thereof. Preferably, the modified xylanase is a Family 11 xylanase. The modified xylanase of the present invention may comprise *Trichoderma reesei* xylanase I or II enzymes, or the *Streptomyces lividans* xylanase B or C enzymes. It is generally recognized that the amino acid sequence of a natural xylanase may be tailored to alter its biochemical or biophysical properties. An example of a modified xylanase of the present invention comprises the X131N mutation, or its equivalent as determined by comparing the sequence alignment of the xylanase of interest with that of TrX II (SEQ ID NO:1) and other modifications, substitutions or deletions relative to the corresponding native xylanase. Several examples of modified xylanases that are not to be considered limiting are shown in Table 2.

The substitution at position 131 to asparagine, in conjunction with a Thr/Ser at position 133, which is highly conserved in Family 11 xylanases, results in the creation of a N-glycosylation motif: Asn-Xaa-Thr/Ser. It has been observed that xylanases comprising the 131N mutation result in an increased production of xylanase. Without wishing to be bound by theory, the introduction of the N-glycosylation motif may result in increased expression efficiency, decreased degradation, increased secretion, or a combination thereof, of the modified xylanase when compared to the native xylanase enzyme lacking the 131N modification. The modified xylanase may exhibit improved expression from a *Trichoderma* host strain and exhibit similar biochemical and biophysical properties, in comparison to the corresponding native Family 11 xylanase. Similar mutations may also be prepared at other sites adjacent to conserved Thr/Ser in xylanase, for example but not limited to X34N, X180N and X182N (ITX 2, ITX 3 and ITX 4, respectively; see Table 2), to produce the Asn-Xaa-Thr/Ser sequence. In each of these locations the amino acid Ser is conserved, and 3-D modelling of the folded protein indicates that these sites would be positioned on the outer surface of the protein. Additional modifications that may be made include X34N-S36T, X180N-S182T or X182N-S184T (ITX5', ITX3' and ITX4', respectively) to produce the glycosylation motif Asn-Xaa-Thr.

Those skilled in the art are aware that amino acid substitutions can be made by a number of methods, for example site-directed or random mutagenesis to alter the primary peptide sequence of the xylanase to produce a consensus N-glycosylation motif. Any suitable method may be used to introduce the X34N, X131N, X180N, X182N, X34N-S36T, X180N-S182T or X182N-S184T mutation into the Family xylanase gene. For example, the N-glycosylation motifs may be introduced by direct substitution of one or more codons within the primary xylanase sequence rather than addition of extra nucleotides encoding the N-glycosylation motif so as to increase the production of the xylanase from the host without changing the biophysical and biochemical properties of the enzyme.

By direct substitution it is meant that the glycosylation site is introduced by introducing specific nucleotide changes within the xylanase coding region that alter the primary peptide sequence without changing its length through the addition or deletion of one or more amino acids.

Figure 5A:
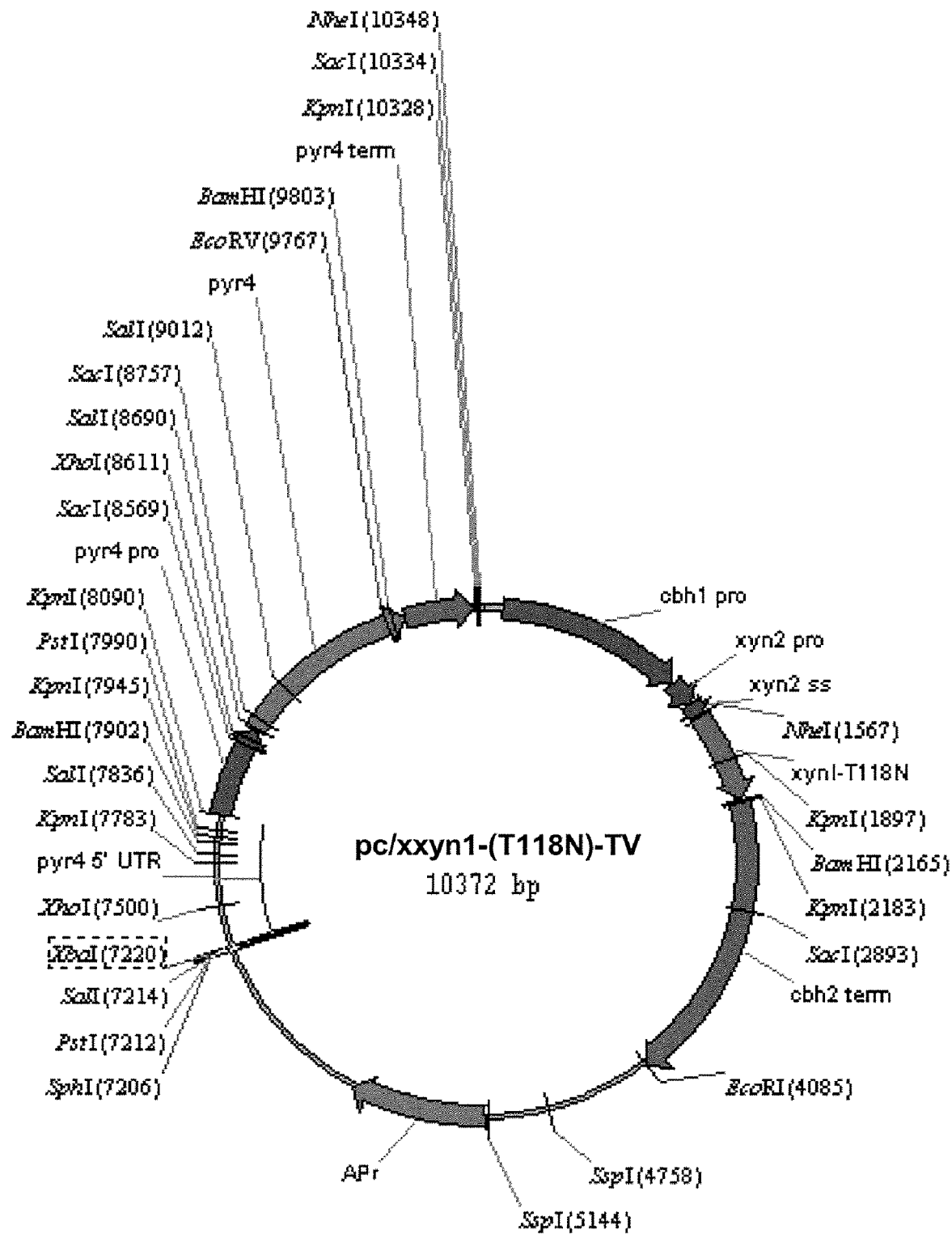
FIG. 5A: pc/xXYN1-(T118N)-TV.
Figure 5B:
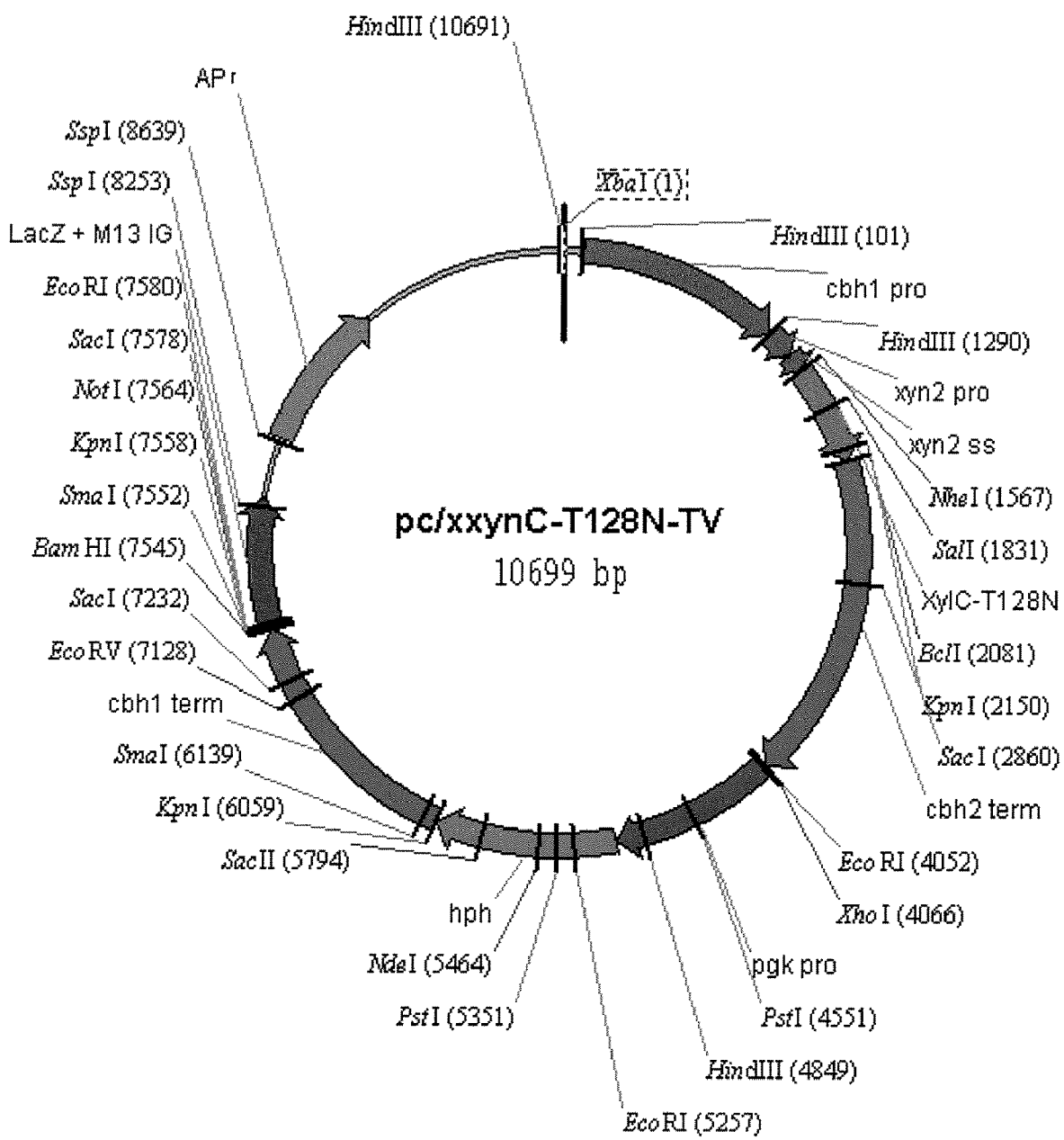
FIG. 5B: pc/xXYLC-(T128N)-TV
Figure 6:
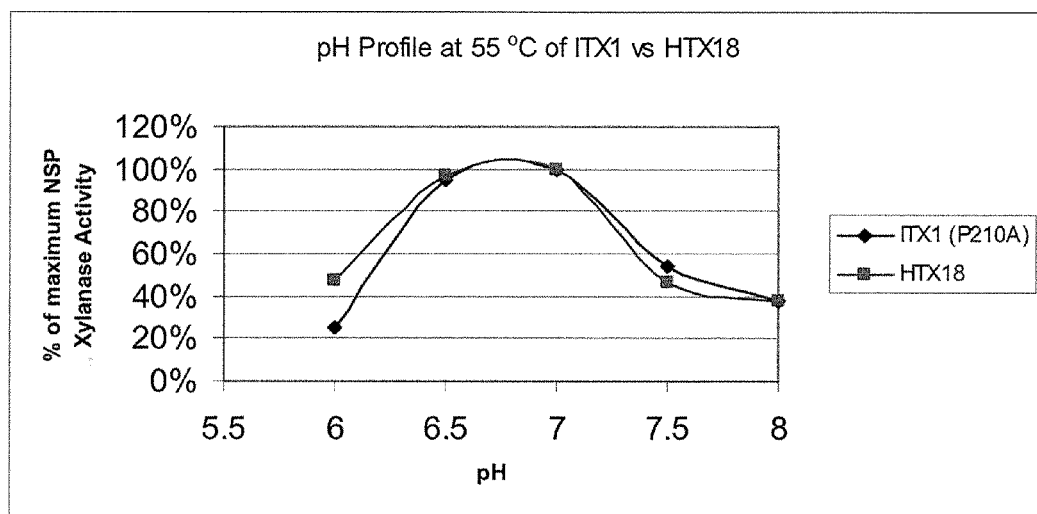
FIG. 6 shows the pH activity profiles for the modified xylanase ITX1, and its native counterpart HTX18.

As shown in Example 11, and with reference to FIGS. 5 and 6, the ITX1 xylanase, comprising the T131N mutation and otherwise having similar mutations as HTX18 (see Table 2; ITX1 lacks the Y135R mutation), has a similar pH and temperature activity profile as the HTX18 xylanase. Thus the addition of the T131N mutation does not alter the biophysical and biochemical properties of the xylanase. Furthermore, as shown in Tables 3 and 4 of Examples 9 and 10, respectively, the ITX1 enzyme is produced with an increase in expression efficiency of about 73%-100% when compared to HTX18 or HTX18(R135Y).

TABLE 2

Examples of Modified xylanases

| Xylanase | Description |
| --- | --- |
| TrX-HML | TrX with N10H, Y27M, and N29L (see U.S. Pat. No. 5,759,840) |
| HTX13 | TrX with N10H, Y27M, N29L, S75A, L105H, S125A, I129E |
| HTX18 | TrX with N10H, Y27M, N29L, S75A, L105H, S125A, I129E, Y135R, H144R, N157D, Q161R, Q162H and Q165R |
| ITX1 | TrX with N10H, Y27M, N29L, S75A, L105H, S125A, I129E, T131N, H144R, N157D, Q161R, Q162H and Q165R |
| ITX2 | TrX with N10H, Y27M, N29L, S75A, L105H, S125A, I129E, T131N, Y135R, H144R, N157D, Q161R, Q162H and Q165R |
| ITX3 | TrX with N10H, Y27M, N29L, S75A, L105H, S125A, I129E, H144R, N157D, Q161R, Q162H, Q165R and F180N |
| ITX3' | TrX with N10H, Y27M, N29L, S75A, L105H, S125A, I129E, H144R, N157D, Q161R, Q162H, Q165R, F180N and S182T |
| ITX4 | TrX with N10H, Y27M, N29L, S75A, L105H, S125A, I129E, H144R, N157D, Q161R, Q162H, Q165R and S182N |
| ITX4' | TrX with N10H, Y27M, N29L, S75A, L105H, S125A, I129E, H144R, N157D, Q161R, Q162H, Q165R, S182N and S184T |
| ITX5 | TrX with N10H, Y27M, N29L, Q34N, S75A, L105H, S125A, I129E, H144R, N157D, Q161R, Q162H and Q165R |
| ITX5' | TrX with N10H, Y27M, N29L, Q34N, S36T, S75A, L105H, S125A, I129E, H144R, N157D, Q161R, Q162H and Q165R |
| HTX18-R135Y | TrX with N10H, Y27M, N29L, S75A, L105H, S125A, I129E, H144R, N157D, Q161R, Q162H and Q165R |
| Xln1(131N) | *T. reesei* xylanase I with mutation T118N |
| *S. lividans* xlnC(131N) | *S. lividans* xylanase C with mutation T128N |

"Expression efficiency" is the amount of active enzyme, or enzymatic activity, produced by a production host. The expression efficiency may be calculated as the quantity of active enzyme or enzymatic activity generated per unit volume of the fermentation culture when all fermentation conditions remain constant. A first xylanase will be considered as having higher expression efficiency compared to a second xylanase if the first xylanase is produced in levels that are higher than a second xylanase by the same host at the same fermentation conditions. For example if the first xylanase is produced at an amount that is greater than about 40% to about 2500%, or an amount there between, than the second xylanase by the same host at the same fermentation conditions, then the expression efficiency of the first xylanase is greater than that the second xylanase. For example, the first xylanase may be produced at an amount that is greater than 40, 50, 60, 70, 80, 90, 100, 110, 120, 130, 140, 150, 160, 170, 180, 190, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1250, 1500, 1750, 2000, 2250, or 2500%, or an amount there between, than the second xylanase by the same host at the same fermentation conditions. Preferably, the first xylanase is produced at an amount that is at least 50% more than the second xylanase by the same host at the same fermentation conditions (see Examples 9 and 10).

By "operatively linked" it is meant that the particular sequences interact either directly or indirectly to carry out an intended function, such as mediation or modulation of gene expression. The interaction of operatively linked sequences may, for example, be mediated by proteins that interact with the operatively linked sequences.

By "xylanase gene" it is meant a region of DNA that includes the sequence that encodes the xylanase enzyme. The xylanase gene may encode a native or a modified xylanase.

A xylanase gene may further comprise a promoter, secretion signal, coding region and transcriptional terminator.

A "xylanase genetic construct" refers to nucleic acid sequence comprising the elements necessary to produce and secrete a native xylanase, or a modified xylanase. Preferably, the xylanase genetic construct is optimized to permit expression from a suitable production host, for example but not limited to, production from a *Trichoderma* host. These elements include:

A Xylanase Coding Region.

A xylanase coding region comprises the DNA sequence necessary to encode a functional xylanase as isolated from extracellular culture filtrates. The xylanase coding region may be comprised of a sequence encoding a native xylanase, a sequence encoding an altered xylanase that has previously been engineered, a modified xylanase as described herein, and a combination thereof. The modified xylanase coding region may include the X34N, X131N, X180N, X182N, X34N-S36T, X180N-S182T or X182N-S184T mutation (TrX II numbering), but does not include a secretion signal at the amino terminal end. The xylanase coding region may be from a Family 11 xylanase gene that has previously been altered (see non-limiting examples provided above, for example but not limited to those disclosed in WO 00/29587, WO 01/92487 and WO 03/046169; which are incorporated herein by reference), or it may be from a natural Family 11 xylanase, for example from a *Trichoderma* or *Streptomyces* gene. For example, but not to be considered limiting, the modified xylanase coding region of the present invention may be derived from a natural or an engineered coding region of *T. reesei* xln1, *T. reesei* xln2, or *S. lividans* xlnC.

As understood by one of skill in the art, a natural coding region can be altered or engineered by replacement, substitution, addition, or elimination of one or more nucleic acids without changing its function (i.e. xylanase activity). The practice of this invention is not constrained by such alterations to the xylanase coding region.

A Secretion Signal.

A "secretion signal" is a peptide sequence present within the secreted protein, typically at the amino terminus of a secreted protein, which directs entry of the protein into the endoplasmic reticulum (ER); the secretion signal may subsequently be cleaved from the mature secreted protein by a signal peptidase.

The coding region of a modified xylanase gene of the present invention may be operably linked to a DNA sequence encoding any secretion signal (i.e., linked in such a manner that the transcribed sequence may be directed to the ER) that is functional in a desired production host, for example, but not limited to, *Trichoderma*. The xylanase secretion signal may, for example, be from any secreted *Trichoderma* protein, for example from a *Trichoderma* xylanase, or from another fungal or bacterial protein. Without wishing to be limiting, the secretion signal may be from the *Trichoderma reesi* xylanase I (xln1) gene or xylanase II (xln2) gene.

Those skilled in the art are aware that a natural secretion signal can be modified by replacement, substitution, addition, or elimination of one or more nucleic acids without changing its function as a secretion signal. The practice of the invention is not constrained by such alterations to the secretion signal.

A Promoter.

The practice of this invention is not constrained by the choice of promoter in the genetic construct. It is preferred that the promoter is functional in the production host. The promoter is operably linked to the coding region of the modified xylanase gene, or it is operatively linked to the secretion signal which is operatively linked to the coding region of the modified xylanase gene, so that the promoter controls the expression of the coding region, or the secretion signal and coding region, respectively. Without wishing to be limiting in any manner, preferred promoters that may be used in the practice of the present invention include the *Trichoderma* cbh1, cbh2, eg1, eg2, eg3, eg5, xln1 and xln2 promoters, or a combination of two or more than two of these promoters.

Those skilled in the art are aware that a natural promoter can be modified by replacement, substitution, addition, or elimination of one or more nucleic acids without changing its function as a promoter. The practice of the invention is not constrained by such alterations to the promoter.

Additional Sequences Between the Secretion Signal and the Mature Xylanase Coding Region.

The xylanase genetic construct may contain additional sequences that encode the additional amino acids between the secretion signal and the xylanase coding region, or the modified xylanase coding region as described herein. These sequences, which may be natural or synthetic, may encode one or more of the amino acids of the mature protein corresponding to the secretion signal encoded by the construct or may result from the addition of restriction enzyme sites needed to join the sequences encoding the secretion signal and modified xylanase coding region. The practice of the invention is not constrained by the presence of additional DNA sequences between those encoding the secretion signal and the mature xylanase coding region.

Other Elements.

The xylanase genetic construct may contain a transcriptional terminator that is functional in the production host, as would be known to one of skill in the art. The transcriptional terminator may be positioned immediately downstream of the xylanase coding region. The practice of the invention is not constrained by the choice of transcriptional terminator that is sufficient to direct the termination of transcription by an RNA polymerase in the production host. An example of a transcriptional terminator which is not to be considered limiting in any manner, comprises 1.9 kb of DNA 3' to the stop codon of the *Trichoderma* cbh2 gene, as described in Examples 5.1-5.4.

The xylanase genetic construct may contain a selectable marker for determining transformation of the production host. The selectable marker may be present on the same plasmid vector, upstream or downstream of the genetic construct (i.e., at the 5' or 3' end of the construct), or the selectable marker may be co-transformed with the construct on a separate plasmid vector.

Choices of selectable markers are well known to those skilled in the art and include genes (synthetic or natural) that confer to the transformed cells the ability to utilize a metabolite that is not normally metabolized by the microbe (e.g., the *A. nidulans* amdS gene encoding acetamidase and conferring the ability to grow on acetamide as the sole nitrogen source) or antibiotic resistance (e.g., the *Escherichia coli* hph gene encoding hygromycin-β-phosphotransferanse and conferring resistance to hygromycin). If the host strain lacks a functional gene for the marker chosen, then that gene may be used as a marker. Examples of such markers include trp, pyr4, pyrG, argB, leu, and the like. The corresponding host strain would therefore have to be lacking a functional gene corresponding to the marker chosen, i.e. lacking in the expression of trp, pyr, arg, leu and the like. A non-limiting example of a selectable marker used in the genetic constructs is described in Example 5.1. In this example, the selectable marker is an *E. coli* hph gene expressed using a *Trichoderma* phosphoglycerate kinase (pgk) promoter. An alternate selectable marker is described in Example 5.2 and comprises the *Neurospora crassa* pyr4 gene expressed from its native promoter.

The present invention provides genetic constructs and genetically modified production hosts, for example *Trichoderma* strains, expressing modified xylanases that introduce or alter a glycosylation site in xylanase. Non-limiting examples of modified xylanases comprising an introduced glycosylation site include one or more than one of X34N, X131N, X180N, X182N, X34N-S36T, X180N-S182T or X182N-S184T mutation (TrX II numbering).

The modified xylanase genetic construct of the present invention is not constrained by the method of making the construct which can include, but is not limited to, standard molecular biology techniques such as isolation of plasmid DNA from *E. coli* by alkaline lysis, digestion of plasmid DNA with restriction endonucleases, separation and isolation of DNA fragments by agarose gel electrophoresis, ligation of DNA fragments with T4 DNA ligase, insertion of unique restriction sites at the ends of DNA fragments by polymerase chain reaction or the addition of oligonucleotide linkers, and the blunting of DNA fragments with T4 DNA polymerase or Klenow fragment of *E. coli* DNA polymerase I. Such a procedure is described in Examples 1-5.

In a further aspect of the present invention, the modified xylanase genetic construct is introduced into and expressed in a desired microbial (production) host. Preferably the expression efficiency for the modified xylanases from the resulting recombinant microbe is increased. For example the expression efficiency may be at least, 40% or more, higher than the expression efficiency for the corresponding Family 11 xylanase produced from the corresponding genetic construct from which the modified xylanase was derived or produced, in the same microbial host grown under similar fermentation conditions. For example, the first xylanase may be produced at an amount that is greater than 40, 50, 60, 70, 80, 90, 100, 110, 120, 130, 140, 150, 160, 170, 180, 190, 200, 250, 300, 350, 400, 425, 450, 474, 500, 525, 550, 575, 600, 625, 650, 675, 700, 725, 750, 775, 800, 825, 850, 875, 900, 925, 950, 975, 1000, 1100, 1250, 1300, 1500, 1750, 2000, 2250, or 2500%, or any amount there between, than the second xylanase by the same host at the same fermentation conditions. Preferably, the first xylanase is produced at an amount that is at least 50% more than the second xylanase by the same host at the same fermentation conditions (see Examples 9 and 10).

The practice of the present aspect of the invention is not constrained by the method of introducing the xylanase genetic construct into the microbial host (production host). Methods of introducing the DNA construct into a production host are familiar to those skilled in the art and include, but are not limited to calcium chloride treatment of bacterial cells or fungal protoplasts to weaken the cell membranes, addition of polyethylene glycol to allow for fusion of cell membranes, depolarization of cell membranes by electroporation, or shooting the DNA through the cell wall and membranes via microprojectile bombardment with a particle gun.

The production host may be a member of the species of Trichoderma (which has been classified at various times as *T. viride, T. longibrachiatum* and, most recently, as *Hypocrea jecorina*-Simmons, 1977; Bissett, 1984; Cannon 1986; Kuhls et al., 1996). These species are well suited because they produce Family 11 xylanases. In addition, methods have been published for the introduction of DNA constructs into cellulase-producing strains of Trichoderma (Lorito et al., 1993; Goldman et al., 1990; Penttila et al., 1987).

Example 7.1 describes one procedure for introducing a xylanase genetic construct into Trichoderma spores using a particle gun. Example 7.2 describes a procedure for introducing a xylanase genetic construct into Trichoderma protoplasts treated with polyethylene glycol and calcium chloride.

An increase in the expression efficiency, for example a 50% enhancement of expression efficiency, over a native Family 11 xylanase, reflects a significant enhancement that is well above the natural variability of the strain and is commercially significant. Results show that the degree of enhancement of xylanase production by this method can be as high as 2-fold and could reach over 10-fold. The measurement of the degree of enhancement of xylanase production is by growth of the culture and measurement of the xylanase activity, as described in Example 8.

It is understood by those skilled in the art that the specific xylanase activity of an enzyme mixture (in IU/mg protein) may be increased by decreasing the amount of cellulase and other proteins in the enzyme mixture. This can be done as desired, by physical and mechanical separation of the enzyme mixture to remove cellulase and other proteins from the mixture, or by deletion of the cellulase or other genes by recombinant means from the production host so that the expression of cellulase or other proteins is reduced or eliminated. Such methods have little or no effect on the actual production of xylanase by the production host.

Xylanases and modified xylanases, as outlined herein, may be used for the purposes of bleaching pulp or other applications requiring activities at temperatures and pH above that of the wild-type enzyme. For the bio-bleaching of pulp, a xylanase derived from a xylanase classified in Family 11 (see Table 1) is most commonly used. The modifications as outlined herein may be found in native xylanase proteins, and these native xylanase enzymes, when expressed in alternate (non-native) production hosts, may exhibit the desired features as described herein, and are included within the present invention.

The practice of the present invention is not constrained by the industrial application of the modified xylanase. Industrial uses of a xylanase produced according to the present invention include, but are not limited to, food processes, for example poultry or swine feed additives, baking or brewing, or industrial processes such as pulp and paper manufacturing.

The following is a summary of the sequences disclosed in the present invention (SEQ ID NOS: 28 to 45 refer to xylanases from the listed organisms (see Table 2 for more details):

| Sequence | Name |
|---|---|
| SEQ ID NO: 1 | TrxII (Tr2) |
| SEQ ID NO: 2 | TrxI (Tr1) |
| SEQ ID NO: 3 | S75A |
| SEQ ID NO: 4 | L105H |
| SEQ ID NO: 5 | S125A |
| SEQ ID NO: 6 | I129E |
| SEQ ID NO: 7 | Y135R |
| SEQ ID NO: 8 | H144R |
| SEQ ID NO: 9 | N157D |
| SEQ ID NO: 10 | Q161R |
| SEQ ID NO: 11 | Q162H |
| SEQ ID NO: 12 | T165H |
| SEQ ID NO: 13 | T131N, R135Y |
| SEQ ID NO: 14 | R135Y |
| SEQ ID NO: 15 | T128N |
| SEQ ID NO: 16 | XynC-5F (Nhe) |
| SEQ ID NO: 17 | XynC-3R (Kpn) |
| SEQ ID NO: 18 | T118N |
| SEQ ID NO: 19 | Xyn1-F |
| SEQ ID NO: 20 | Xyn1-R (BamHI) |
| SEQ ID NO: 21 | T131N |
| SEQ ID NO: 22 | F180N |
| SEQ ID NO: 23 | F180N, S182T |
| SEQ ID NO: 24 | S182N |
| SEQ ID NO: 25 | S182N, S184T |
| SEQ ID NO: 26 | Q34N |
| SEQ ID NO: 27 | Q34N, S36T |
| SEQ ID NO: 28 | *Aspargillus awamori* var. *kawachi* |
| SEQ ID NO: 29 | *Aspergillus tubigensis* |
| SEQ ID NO: 30 | *Bacillus circulans* |
| SEQ ID NO: 31 | *Bacillus pumilus* |
| SEQ ID NO: 32 | *Bacillus subtilis* |
| SEQ ID NO: 33 | *Clostridium acetobutylicum* |
| SEQ ID NO: 34 | *Clostridium stercorarium* |
| SEQ ID NO: 35 | *Ruminococcus flavefaciens* |
| SEQ ID NO: 36 | *Schizophyllum commune* |
| SEQ ID NO: 37 | *Streptomyces* sp. No. 36a |
| SEQ ID NO: 38 | *Streptomyces lividans* |
| SEQ ID NO: 39 | *Streptomyces lividans* |
| SEQ ID NO: 40 | *Thermomonospora fusca* |
| SEQ ID NO: 41 | *Trichoderma harzianum* |
| SEQ ID NO: 42 | *Trichoderma viride* |
| SEQ ID NO: 43 | *Aspergillis niger* |
| SEQ ID NO: 44 | *Aspergillis kawachii* |
| SEQ ID NO: 45 | *Fibrobacter succinogenes* |
| SEQ ID NO: 46 | *Thermomyces lanuginosus* |

The present invention will be further illustrated in the following examples.

EXAMPLES

Example 1 describes the isolation of genomic DNA from *Trichoderma reesi* strain M2C38 and the genetically modified derivatives of these strains. Examples 2-5 describe the construction of genomic DNA libraries, the cloning of various genes, the modification of xylanase gene sequences and several genetic constructs for expression of modified xylanases from *Trichoderma reesei* strains RutC30 and M2C38. Examples 7-10 describe the transformation and expression of xylanase genetic constructs in *Trichoderma reesei* strains and M2C38. Examples 11 and 12 describe the biochemical characterization of modified and native xylanases.

Example 1

Isolation of *Trichoderma reesei* Genomic DNA and Construction of *T. reesei* Genomic Libraries

*Trichoderma reesei* strain M2C38 is a proprietary strain of Iogen Corporation derived from *Trichoderma reesei* RutC30 (ATCC #56765; Montenecourt and Eveleigh, 1979), which was in turn derived from *Trichoderma reesei* Qm6A (ATCC # 13631; Mandels and Reese, 1957). It is well understood by those skilled in the art that the procedures described herein, the genetic constructs from these strains, and the expression of the genetic constructs in these strains is applicable to all *Trichoderma* strains derived from Qm6A.

To isolate genomic DNA, 50 ml of Potato Dextrose Broth (Difco) was inoculated with *T. reesei* spores collected from a Potato Dextrose Agar plate with a sterile inoculation loop. The cultures were shaken at 200 rpm for 2-3 days at 28° C. The mycelia was filtered onto a GFA glass microfibre filter (Whatman) and washed with cold, deionized water. The fungal cakes were frozen in liquid nitrogen crushed into a powder with a pre-chilled mortar and pestle; 0.5 g of powdered biomass were resuspended in 5 ml of 100 mM Tris, 50 mM EDTA, pH 7.5 plus 1% sodium dodecyl sulphate (SDS). The lysate was centrifuged (5000 g for 20 min, 4° C.) to pellet cell debris. The supernatent was extracted with 1 volume buffer (10 mM Tris, 1 mM EDTA, pH 8.0) saturated phenol followed by extraction with 1 volume of buffer-saturated phenol:chloroform:isoamyl alcohol (25:24:1) in order to remove soluble proteins. DNA was precipitated from the solution by adding 0.1 volumes of 3 M sodium acetate, pH 5.2 and 2.5 volumes of cold 95% ethanol. After incubating for at least 1 h at –20° C., the DNA was pelleted by centrifugation (5000 g for 20 min, 4° C.), rinsed with 10 ml 70% ethanol, air-dried and resuspended in 1 ml 10 mM Tris, 1 mM EDTA, pH8.0. RNA is digested by the addition of Ribonuclease A (Boehringer Mannheim) added to a final concentration of 0.1 mg/ml and incubation at 37° C. for 1 hour. Sequential extractions with 1 volume of buffer-saturated phenol and 1 volume of buffer-saturated phenol:chloroform:isoamyl alcohol (25:24:1) are used to remove the ribonuclease from the DNA solution. The DNA is again precipitated with 0.1 volumes of 3M sodium acetate, pH 5.2 and 2.5 volumes of cold 95% ethanol, pelleted by centrifugation, rinsed with 70% ethanol, air-dried and resuspended in 50 µl of 10 mM Tris, 1 mM EDTA, pH 8.0. The concentration of DNA was determined by measuring the absorbance of the solution at 260 nm (p. C1 in Sambrook et al., 1989).

Two plasmid libraries and one phage library were constructed using genomic DNA isolated from *T. reesei* strain M2C38. The plasmid libraries were constructed in the vector pUC119 (Viera and Messing, 1987) as follows: 10 µg genomic DNA was digested for 20 hrs at 37° C. in a 100 µl volume with 2 units/µg of HindIII, BamHI or EcoRI restriction enzymes. The digested DNA was fractionated on a 0.75% agarose gel run in 0.04M Tris-acetate, 1 mM EDTA and stained with ethidium bromide. Gel slices corresponding to the sizes of the genes of interest (based on published information and Southern blots) were excised and subjected to electro-elution to recover the DNA fragments (Sambrook et al., pp. 6.28-6.29). These enriched fractions of DNA were ligated into pUC119 in order to create gene libraries in ligation reactions containing 20-50 µg/ml DNA in a 2:1 molar ratio of vector:insert DNA, 1 mM ATP and 5 units T4 DNA ligase in a total volume of 10-15 µl at 4° C. for 16 h. *Escherichia coli* strain HB101 was electroporated with the ligation reactions using the Cell Porator System (Gibco/BRL) following the manufacturer's protocol and transformants selected on LB agar containing 70 µg/ml amplicillin.

The phage library was constructed in the lambda vector λDASH (Stratagene, Inc.) as follows: genomic DNA (3 µg) was digested with 2, 1, 0.5 and 0.5 units/µg Bam HI for 1 hour at 37° C. to generate fragments 9-23 kB in size. The DNA from each digest was purified by extraction with 1 volume Tris-staturated phenol:choroform:isoamyl alcohol (25:24:1) followed by precipitation with 10 µl 3M sodium acetate, pH 5.2 and 250 µl 95% ethanol (–20° C.). The digested DNA was pelleted by microcentrifugation, rinsed with 0.5 ml cold 70% ethanol, air-dried and resuspended in 10 µl sterile, deionized water. Enrichment of DNA fragments 9-23 kB in size was confirmed by agarose gel electrophoresis (0.8% agarose in 0.04 M Tris-acetate, 1 mM EDTA). Digested DNA (0.4 µg) was ligated to 1 µg λDASH arms predigested with BamHI (Stratagene) in a reaction containing 2 units T4 DNA ligase and 1 mM ATP in a total volume of 5 µl at 4° C. overnight. The ligation mix was packaged into phage particles using the GigaPack® II Gold packaging extracts (Stratagene) following the manufacturer's protocol. The library was titred using the *E. coli* host strain XL1-Blue MRA (P2) and found to contain $3 \times 10^5$ independent clones.

Example 2

Isolation of Genomics Clones from *T. reesei* M2C38 Libraries 2.1 Cloning the Cellobiohydrolase I (cbh1) and Cellobiohydrolase II (cbh2) Genes from pUC119 Libraries

*E. coli* HB101 transformants harboring cbh1 or cbh2 clones from recombinant pUC119-BamHI or -EcoRI libraries were identified by colony lift hybridization: $1-3 \times 10^4$ colonies were transferred onto HyBond™ nylon membranes (Amersham); membranes were placed colony-side up onto blotting paper (VWR 238) saturated with 0.5 M NaOH; 1 M NaCl for 5 min to lyse the bacterial cells and denature the DNA; the membranes were then neutralized by placing them colony-side up onto blotting paper (VWR 238) saturated with 1.5 M Tris, pH 7.5 plus 1 M NaCl for 5 min; the membranes were allowed to air-dry for 30 min and the DNA was then fixed to the membranes by baking at 80° C. for 2 h.

$^{32}$P-labelled probes were prepared by PCR amplification of short (0.7-1.5 kB) fragments of the cbh1 and cbh2 coding regions from the enriched pool of BamHI or EcoRI fragments, respectively, in a labelling reaction containing 10-50 ng target DNA, 0.2 mM each d(GCT)TP, 0.5 µM dATP, 20-40 µCi α-$^{32}$P-dATP, 10 pmole oligonucleotide primers and 0.5 units Taq polymerase in a total volume of 20 µl. The reaction was subjected to 6-7 cycles of amplification (95° C., 2 min; 56° C., 1.5 min; 70° C., 5 min). The amplified, $^{32}$P-labelled DNA was precipitated by the addition of 0.5 ml 10% (w/v) trichloroacetic acid and 0.5 mg yeast tRNA. The DNA was pelleted by microcentrifugation, washed twice with 1 ml 70% ethanol, air-dried and resuspended in 1M Tris pH7.5, 1 mM EDTA.

Nylon membranes onto which the recombinant pUC119 plasmids had been fixed were prehybridized in heat-sealed bags for 1 h at 60-65° C. in 1 M NaCl, 1% SDS, 50 mM Tris, 1 mM EDTA pH 7.5 with 100 µg/ml denatured sheared salmon sperm DNA. Hybridizations were performed in heat-sealed bags in the same buffer with only 50 μg/ml denatured sheared salmon sperm DNA and 5×10$^6$-5×10$^7$ cpm of denatured bgl1, cbh1 or cbh2 probe for 16-20 h at 60-65° C. Membranes were washed once for 15 min with 1 M NaCl, 0.5% SDS at 60° C., twice for 15 min each with 0.3M NaCl, 0.5% SDS at 60° C. and once for 15 min with 0.03M NaCl, 0.5% SDS at 55° C. Membranes were again placed in heat-sealed bags and exposed to Kodak RP X-ray film for 16-48 h at −70° C. The X-ray film was developed following the manufacturer's protocols. Colonies giving strong or weak signals were picked and cultured in 2×YT media supplemented with 70 μg/ml ampicillin. Plasmid DNA was isolated from these cultures using the alkaline lysis method (Sambrook, et al., pp. 1.25-1.28) and analyzed by restriction digest, Southern hybridization (Sambrook, et al., pp. 9.38-9.44) and PCR analysis (Sambrook, et al., pp. 14.18-14, 19).

Clones carrying the cbh1 gene were identified by colony lift hybridization of the pUC119-BamHI library with a 0.7 kb cbh1 probe prepared using oligonucleotide primers designed to amplify bp 597-1361 of the published cbh1 sequence (Shoemaker et al., 1983). A cbh1 clone, pCOR132 was isolated containing a 5.7 kb BamHI fragment corresponding to the promoter (4.7 kb) and 1 kb of the cbh1 structural gene (2.3 kb). From this, a 2.5 kb EcoRI fragment containing the cbh1 promoter (2.1 kb) and 5' end of the cbh1 coding region (0.4 kb) was subcloned into pUC119 to generate pCB152. Clones carrying the cbh2 gene were identified by colony lift hybridization of the pUC119-EcoRI library with a 1.5 kb cbh2 probe prepared using oligonucleotide primers designed to amplify bp 580-2114 of the published cbh2 sequence (Chen et al. 1987). A cbh2 clone, pZUK600 was isolated containing a 4.8 kb EcoRI fragment corresponding to the promoter (600 bp), structural gene (2.3 kb) and terminator (1.9 kb).

2.1 Cloning cbh1 Terminator, Xylanase II (xln2) Gene, and Phosphoglycerate Kinase Promoter (pgk p) from λDASH Libraries Digoxigen-11-dUTP labelled probes were prepared from PCR amplified coding regions of the cbh1, xln2 and pgk genes by random prime labelling using the DIG Labelling and Detection kit (Boehringer Mannheim) and following the manufacturer's protocols. Genomic clones containing the cbh1, xln2 and pgk genes were identified by plaque-lift hybridization of the λDASH library. For each gene of interest, 1×10$^4$ clones were transferred to Nytran® (Schleicher and Schull) nylon membranes. The phage particles were lysed and the phage DNA denatured by placing the membranes plaque-side up on blotting paper (VWR238) saturated with 0.5 M NaOH, 1 M NaCl for 5 min; the membranes were then neutralized by placing them plaque-side up onto blotting paper saturated with 1.5 M Tris, pH 7.5 plus 1 M NaCl for 5 min; the membranes were allowed to air-dry for 30 min and the DNA was then fixed to the membranes by baking at 80° C. for 2 h. The membranes were prehybridized in heat-sealed bags in a solution of 6×SSPE, 5×Denhardt's, 1% SDS plus 100 μg/ml denatured, sheared salmon sperm DNA at 65° C. for 2 h. The membranes were then hybridized in heat-sealed bags in the same solution containing 50 μg/ml denatured, sheared salmon sperm DNA and 0.5 μg of digoxigen-dUTP labelled probes at 65° C. overnight. The membranes were washed twice for 15 min in 2×SSPE, 0.1% SDS at RT, twice for 15 min in 0.2×SSPE, 0.1% SDS at 65° C. and once for 5 min in 2×SSPE. Positively hybridizing clones were identified by reaction with an anti-digoxigenin/alkaline phosphatase antibody conjugate, 5-bromo-4-chloro-3-indoyl phosphate and 4-nitro blue tetrazolium chloride (Boehringer Mannheim) following the manufacturer's protocol. Positively hybridizing clones were further purified by a second round of screening with the digoxigen-dUTP labelled probes.

Individual clones were isolated and the phage DNA purified as described in Sambrook et al. (1989) pp. 2.118-2.121 with the exception that the CsCl gradient step was replaced by extraction with 1 volume of phenol:choroform:isoamyl alcohol (25:24:1) and 1 volume of chloroform:isoamyl alcohol (24:1). The DNA was precipitated with 0.1 volumes of 3M sodium acetate, pH 5.2 and 2.5 volumes cold 95% ethanol. The precipitated phage DNA was washed with 0.5 ml cold 70% ethanol, air-dried and resuspended in 50 μl 10 mM Tris, 1 mM EDTA pH8.0. Restriction fragments containing the genes of interest were identified by restriction digests of the purified phage DNA and Southern blot hybridization (Sambrook, et al., pp. 9.38-9.44) using the same digoxigen-dUTP labelled probes used to screen the λDASH library. The membranes were hybridized and positively hybridizing fragments visualized by the same methods used for the plaque lifts. Once the desired restriction fragments from each λDASH clone were identified, the restriction digests were repeated, the fragments were resolved on a 0.8% agarose gel in TAE and the desired bands excised. The DNA was eluted from the gel slices using the Sephaglas B and Prep Kit (Pharmacia) following the manufacturer's protocol.

Clones carrying the cbh1 gene were identified by colony lift hybridization of the λDASH library (Example 2) with a cbh1 probe comprising bp 45-2220 of the published cbh1 sequence (Shoemaker et al.). A 1.8 kb BamHI fragment containing the 3' end of the cbh1 coding region (0.5 kb) and the cbh1 terminator (1.3 kb) was isolated by restriction digestion of phage DNA purified from a λDASH cbh1 clone. This fragment was subcloned into the BamHI site of the E. coli plasmid vector pUC119 to generate the plasmid pCB1Ta. Clones carrying the xln2 gene were identified by colony lift hybridization of the λDASH library (Example 2) with a xln2 probe comprising bp 100-783 of the published xln2 sequence (Saarelainen et al., 1993). A 5.7 kb KpnI fragment containing the promoter (2.3 kb), coding region (0.8 kb) and terminator (2.6 kb) the xln2 gene was isolated by restriction digestion of phage DNA purified from a λDASH xln2 clone. This fragment was subcloned into the KpnI site of pUC119 to generate the plasmid pXYN2K-2. Clones carrying the pgk gene were identified by colony lift hybridization of the λDASH library (Example 2) with a pgk1 probe comprising bp 4-1586 the published pgk sequence (Vanhanen et al., 1989). A 5.0 kb EcoRI fragment containing the promoter (2.9 kb), coding region (1.6 kb) and terminator (0.5 kb) the pgk gene was isolated by restriction digestion of phage DNA purified from a λDASH pgk clone. This fragment was subcloned into the EcoRI site of pUC119 to generate the plasmid pGK5.0.

Example 3

Cloning and Modification of the T. reesei Xylanase I and S. lividans Xylanase C Genes Xylanase C (xylC; SEQ ID NO:39) was amplified from genomic DNA isolated from Streptomyces lividans using primers that introduced a NheI site upstream and a KpnI site downstream of the coding sequence. Megaprimer PCR was used to introduce the T128N mutation into xylC. The mutagenic primer was used in conjunction with the reverse primer to introduce a KpnI site downstream. The resulting PCR product was isolated and used as a reverse primer in conjunction with the forward primer to introduce a NheI site upstream. The sequence of the modified *S. lividans* xylanase C is shown in SEQ ID NO: 48). Primer sequences are listed below:

```
T128N:
CCCTCCGTGG AAGGCAACAA GACCTTCCAG  (SEQ ID NO: 15)

XynC-5F(Nhe):
GCCCACGCCG CTAGCACCAT CACC        (SEQ ID NO: 16)

XynC-3R(Kpn):
CGTCCACCGG TACCAGGTCA ACC         (SEQ ID NO: 17)
```

The gene encoding xylanase I (xynI; SEQ ID NO:2) was amplified from genomic DNA isolated from *T. ressei* strain M2C38 using primers that introduced a NheI site upstream and a BamHI site downstream of the coding sequence. Megaprimer PCR was used to introduce the T118N mutation into xynI. The mutagenic primer was used in conjunction with the reverse primer to introduce a BamHI site downstream. The resulting PCR product was isolated and used as a reverse primer in conjunction with the forward primer to introduce a NheI site upstream. The sequence of the modified *T. ressei* xylanase C is shown in SEQ ID NO: 47). Primer sequences are listed below:

```
T118N:   CCATCCAGGG CAACGCGACC TTC   (SEQ ID NO: 18)

XynI-F:  CGTCGTGCTA GCATCAACTA CGAC  (SEQ ID NO: 19)

XynI-R   GGATCCTAGT TGCTGACAC        (SEQ ID NO: 20)
(BamHI):
```

The amino acid sequences for the native, unmodified *T. reesei* xylanase I and *S. lividans* xylanase C encoded by the genetic constructs described in Examples 5.4 and 5.5 are provided as SEQ ID NO: 2 and SEQ ID NO: 39, respectively.

Example 4

Mutagenesis of *T. reesei* Xylanase II to Generate the Variants HTX18, ITX1-5, ITX3'-5', HTX18(R135Y)

4.1 Introduction of Mutations N10H, 27M, Y29L

Genetic engineering of the xln2 gene from strain M2C38 was performed by cassette mutagenesis of a synthetic xln2 gene (Sung et al., 1995; also see WO 01/92487 and WO 03/046169; which are incorporated herein by reference). Specifically, a double-stranded ApaI/PinAI fragment comprising codons 8-33, in which codons 10, 27 and 29 were altered as indicated in SEQ ID: 2, was synthesized in vitro. This fragment was then used to replace the native xln2 sequence in the plasmid pUC/Xln (Sung et al., 1993). The synthetic DNA comprising codons 32-190 in pUC/XLN was replaced by the corresponding genomic fragment of *T. reesei* xln2, containing a 108 bp intron at codon 58, which was amplified using genomic *T. reesei* DNA as a template and introducing a unique PinAI site at codons 31 and 32 and a unique BamHI directly downstream of the TAG stop codon. This generates pUC/HTX4.

4.2 Introduction of Mutations 75A, 105H, 125A, 129E

A 3.2 kb SstI fragment containing the promoter regions, the xln2 gene, and part of the cbh2 terminator was isolated from pC/XHML-TV (see example 5.1, below) and cloned into the SstI site in the polylinker of the mutagenesis vector, pALTER®-1 (Promega). Four sequential rounds of mutagenesis were performed to alter specific amino acids using primers specifically designed to incorporate the desired mutations:

```
                                          (SEQ ID NO: 3)
     S75A:   AGCTACCTCG CCGTGTACGG, (SEQ ID NO: 4)
     L105H:  CCACCAAGCA CGGCGAGGT, (SEQ ID NO: 5)
     S125A:  ACGCAGCGCG TCAACGCCCC GTCCATCATC GGC,
     and (SEQ ID NO: 6)
     I129E:  AACGCCCCGT CCATCGAGGG CACCGCCACC TTT
```

Figure 3:
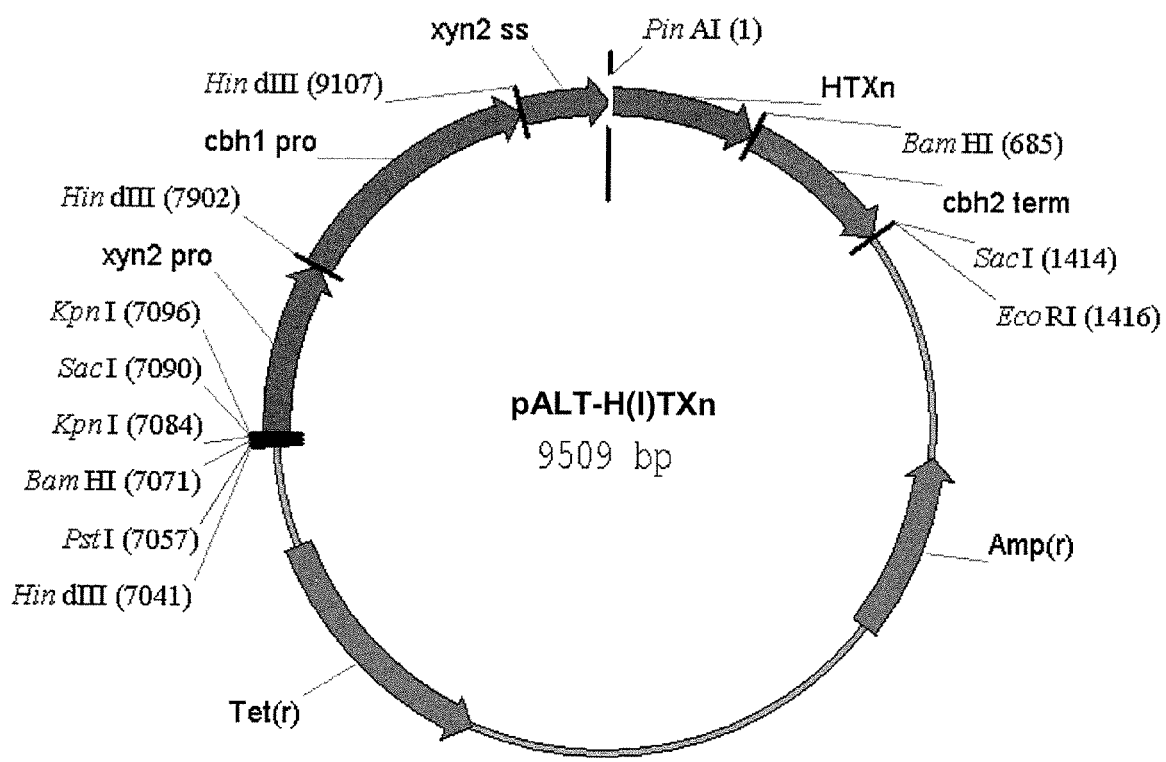
FIG. 3 shows a map of the general mutagenesis vector pALT-H(I)TXn, where "n" is a descriptor, for example "13" or "18", and the vector may comprise a 131 N mutation (i.e., pALT-ITXn), or the vector may not comprise a 131N mutation (i.e., pALT-HTXn). For example when "n" is 18, and the vector does not comprise the 131N mutation, the vector is pALT-HTX18.

(see WO 01/92487 and WO 03/046169; which are incorporated herein by reference, for associated methods); this generated the plasmid pALT-HTX13 (the plasmid is shown in its generic form, "pALT-H(I)TXn" in FIG. 3. The incorporation of all mutations was verified by DNA sequence analysis.

4.3 Introduction of Mutations Y135R, H144R, N157D, Q161R, Q162H and T165H

Four sequential rounds of mutagenesis were performed on the plasmid pALT-HTX13 using the Promega Altered Sites® II in vitro Mutagenesis System to introduce the six targeted amino acid substitutions and generate pALT-HTX18, as follows:

addition of the 135R and 144R mutations to pALT-HTX13 using primer sequences:

```
Y135R:
GGCACCGCCA CCTTTCGCCA GTACTGGTCC    (SEQ ID NO: 7)
and

H144R:
GTCCGCCGCA ACCGCCGCTC GAGCGGCTC     (SEQ ID NO: 8)
``` to make pALT-HTX13+135R/144R;
addition of the 157D and 162H mutations to pALT-HTX13+135R/144R using primer sequences:

```
N157D:    AACCACTTCG ACGCGTGG       (SEQ ID NO: 9)
and

Q162H:    GGCTCAGCAC GGCCTGACG,     (SEQ ID NO: 11)
``` to make pALT-HTX13+135R/144R/157D/162H;
addition of the 161R mutation to pALT-HTX13+135R/144R/157D/162H using the primer sequence

```
                                          (SEQ ID NO: 10)
     Q161R:  TTCGACGCGT GGGCTCGCCA CGGCCTGACG CTC,
``` to make pALT-HTX13+135R/144R/157D/161R/162H;
addition of the 165H mutation to pALT-HTX13+135R144R157D/161R/162H using the primer sequence

```
                                          (SEQ ID NO: 12)
     T165H:  GCTCGCCACG GCCTGCACCT CGGGACGATG GAT,
``` to make pALT-HTX 18. The plasmid is shown in its generic form, "pALT-H(I)TXn" in FIG. 3. The incorporation of all mutations was verified by DNA sequence analysis.

4.4 Reversion of Mutation Y135R and Introduction of T131N into HTX18

One round of mutagenesis was performed on the plasmid pALT-HTX18 using the Promega Altered Sites® II in vitro Mutagenesis System and the primer sequence:

```
T131N, R135Y:
GGCAACGCCA CCTTTTACCA GTACTGGTCC    (SEQ ID NO: 13)
``` to introduce the T131N and R135Y mutations and generate pALT-ITX1. The plasmid is shown in its generic form, "pALT-H(I)TXn" in FIG. 3. The incorporation of all mutations was verified by DNA sequence analysis

4.5 Reversion of the Y135R Mutation in HTX18

One round of mutagenesis was performed on the plasmid pALT-HTX18 using the Promega Altered Sites® II in vitro Mutagenesis System and the primer sequence:

```
R135Y:
GGCACCGCCA CCTTTTACCA GTACTGGTCC,   (SEQ ID NO 14)
``` to introduce the R135Y mutations and generate pALT-HTX18R135Y. The plasmid is shown in its generic form, "pALT-H(I)TXn" in FIG. 3. The incorporation of all mutations was verified by DNA sequence analysis

4.6 Introduction of Glycosylation Sites at Positions 34, 131, 180 and 182 within HTX18:

One round of mutagenesis was performed on the plasmid pALT-HTX18 using the Promega Altered Sites® II in vitro Mutagenesis System and the primer sequences:

```
T131N:
CCGTCCATCG AGGGCAACGC CACCTTTCGC    (SEQ ID NO: 21)

F180N:
GTGGAGGGTT ACAACAGCTC TGGCTCTGCT    (SEQ ID NO: 22)

F180N, S182T:
GTGGAGGGTT ACAACAGCAC CGGCTCTGCT    (SEQ ID NO: 23)

S182N:
GGTTACTTTA GCAACGGCTC TGCTTCCATC    (SEQ ID NO: 24)

S182N, S184T:
GGTTACTTTA GCAACGGCAC CGCTTCCATC    (SEQ ID NO: 25)

Q34N:
GGTCCCGGCG GGAACTTCTC CGTCAACTGG    (SEQ ID NO: 26)

Q34N, S36T:
GGTCCCGGCG GGAACTTCAC CGTCAACTGG    (SEQ ID NO: 27)
``` to generate the plasmids pALT-ITXn and pALT-ITXn' (where n equals 2 through 5). A generic map of these plasmids, "pALT-H(I)TXn", is shown in FIG. 3. The incorporation of all mutations was verified by DNA sequence analysis

Example 5

Construction of Vectors Directing the Expression of Native and Modified Family 11 Xylanases in *Trichoderma reesei*

5.1 Construction of pC/XHML-TV

A 2.4 kb fragment containing the promoter and secretion signal of the xln2 gene (bp −2150 to +195 where +1 indicates the ATG start codon and +193-195 represent codon 32) was amplified with Pwo polymerase from the genomic xln2 subclone pXYN2K-2 using a xln2-specific primer containing a PinAI at bp 190-195 or codons 31 and 32 and the pUC reverse primer (Cat. No. 18432-013, Gibco/BRL) which anneals downstream of the KpnI site at the 5' end of the xln2 gene. This xln2 PCR product was inserted as a blunt-ended fragment into the SmaI site of the pUC119 polylinker in such an orientation that the BamHI site of the polylinker is 3' to the PinAI site; this generated the plasmid pUC/XynPSS(Pin). The same xln2 PCR product was reisolated from pUC/XynPSS(Pin) by digestion with EcoRI (which was amplified as part of the pUC119 polylinker from pXYN2K-2) and BamHI and inserted into the plasmid pBR322L (a derivative of pBR322 containing an SphI-NotI-SalI adaptor between the original SphI and SalI sites at bp 565 and 650), also digested with EcoRI and BamHI, to generate the plasmid pBR322LXP. To facilitate high level expression of the HTX4 xylanase, a 1.3 kb HindIII fragment comprising bp −1400 to −121 of the xln2 promoter in pBR322LXP was replaced with a 1.2 kb HindIII fragment comprising bp −1399 to −204 of the cbh1 promoter which was isolated by HindIII digestion of pCOR132; this generated the plasmid pBR322LXC. Finally, the EcoRI site of pBR322LXC was then blunted with Klenow and SpeI linkers (Cat. No. 1086, New England Biolabs) were added to generate pBR322SpXC.

A fragment containing codons 1-190 of the xylanase gene containing the mutations N10H, Y27M, N29L was isolated from the plasmid pUC/HTX4 (described in example 4.1, above) by digestion with NheI and BamHI inserted into pCB219N-N digested with NheI and BamHI to generate pHTX4/C2ter. To make pCB219N-N, a cbh2 terminator fragment was amplified from the pZUK600 (described in Example 2, above) template using a primer homologous to bp 2226-2242 of the published 3' untranslated region of the cbh2 gene (Chen et al., 1987) containing a short polylinker comprising XbaI-NheI-BamHI-SmaI-KpnI sites at the 5' end and the pUC forward primer (Cat. No. 1224, New England Biolabs) which anneals upstream of the EcoRI site at the 3' end of cbh2 in pZUK600. This fragment was digested at the engineered XbaI and EcoRI sites and inserted into the corresponding sites of pUC119 to generate pCB219. An EcoRI-NotI adaptor (Cat. No. 35310-010, Gibco/BRL) was inserted into the unique EcoRI site of pCB219 to generate pCB219N. A 2.7 kb fragment comprising codons 9-190 of the HTX4 gene and the cbh2 terminator was isolated from pHTX4/C2ter by digestion with PinAI and NotI and inserted into pBR322SpXC digested with PinAI and NotI to generate the expression cassette pXHML-EC.

The *E. coli* hygromycin phosphotransferase gene (hph) used as a selectable marker for *T. reesei* was amplified with Pwo polymerase from the plasmid pVU1005 (Van den Elzen et al., 1989). The primers were designed to introduce SphI and KpnI sites at the 5' and 3' ends of the hph coding region (bp 211-1236 of the published hph sequence, Gritz and Davies, 1983), respectively. The PCR product was digested with SphI and KpnI and inserted into the corresponding sites in the polylinker region of pUC119. The resulting plasmid, pHPT100, was used as the starting plasmid for the construction of the selection cassette.

Two new linker regions were introduced into plasmid pHPT100 to facilitate the cloning of the promoter and terminator fragments. A HindIII-XbaI-XhoI-SphI linker was inserted between the HindIII and SphI sites as well as a KpnI-NotI-SacI linker which was inserted between the KpnI and SacI sites of pUC119 polylinker remaining in pHPT100. This construct was designated as pHPT 102. The primers used to amplify the pgk promoter (Vanhanen et al., 1991) were designed to introduce an XhoI site and a SphI site at positions −970 and +1 of the promoter respectively. These sites were subsequently used to insert the pgk promoter into the XhoI and SphI sites of pHPT102 to generate pHPT115. A 1.3 kb cbh1 terminator fragment was amplified with Pwo polymerase from pCB1Ta using a primer annealing to the 3' untranslated region of cbh1(bp 1864-1899 of the published cbh1 sequence) containing a KpnI site at bp 1877-1882 and the pUC reverse primer (Cat. No., 18432-013, Gibco/BRL) which anneals downstream of the EcoRI site at the 3' end of the cbh1 terminator in pCB1Ta. The cbh1 terminator PCR product was digested with KpnI and inserted into the unique KpnI site of pHPT115 to generate the selection cassette plasmid pHPT136. The cbh1 terminator in the selection cassette plasmid pHPT136 was replaced with a 2.6 kb KpnI fragment containing the xln2 transcriptional terminator. The xln2 terminator was amplified with Pwo polymerase from the genomic subclone pXYN2K-2 using a primer to introduce a KpnI site directly downstream of bp 780 of the published xln2 sequence (Saarelainen et al. 1993) and the pUC forward primer (Cat. No. 18431-015, Gibco/BRL) which anneals downstream of the 3' end of the xln2 gene in pXYN2K-2. The xln2 terminator PCR product was digested with KpnI and ligated to a 5.1 kb KpnI fragment from pHPT136 containing the pgk promoted-hph gene in pUC119 to generate the selection cassette plasmid pHPT136X, thus maintaining the unique NotI site at the 3' end of the selection cassette.

To make the transformation vector, the expression cassette from pC/XHML-EC was isolated by NotI digestion, blunting the NotI site with Klenow DNA polymerase, and SpeI digestion. At the same time, the selection cassette plasmid was prepared to accept this fragment by digestion with XhoI, blunting of the XhoI site with Klenow DNA polymerase and subsequent digestion with XbaI. The SpeI-expression cassette-NotI° fragment was inserted between the XbaI and XhoI° sites upstream of the selection cassette of pHPT136X. The final transformation vector, pC/XHML-TV (FIG. 2), was linearized by digestion with NotI prior to introduction into *T. reesei* M2C38 via microprojectile bombardment as described in Example 7.

5.2 Construction of pC/XH(I)TXn-TV

Figure 4:
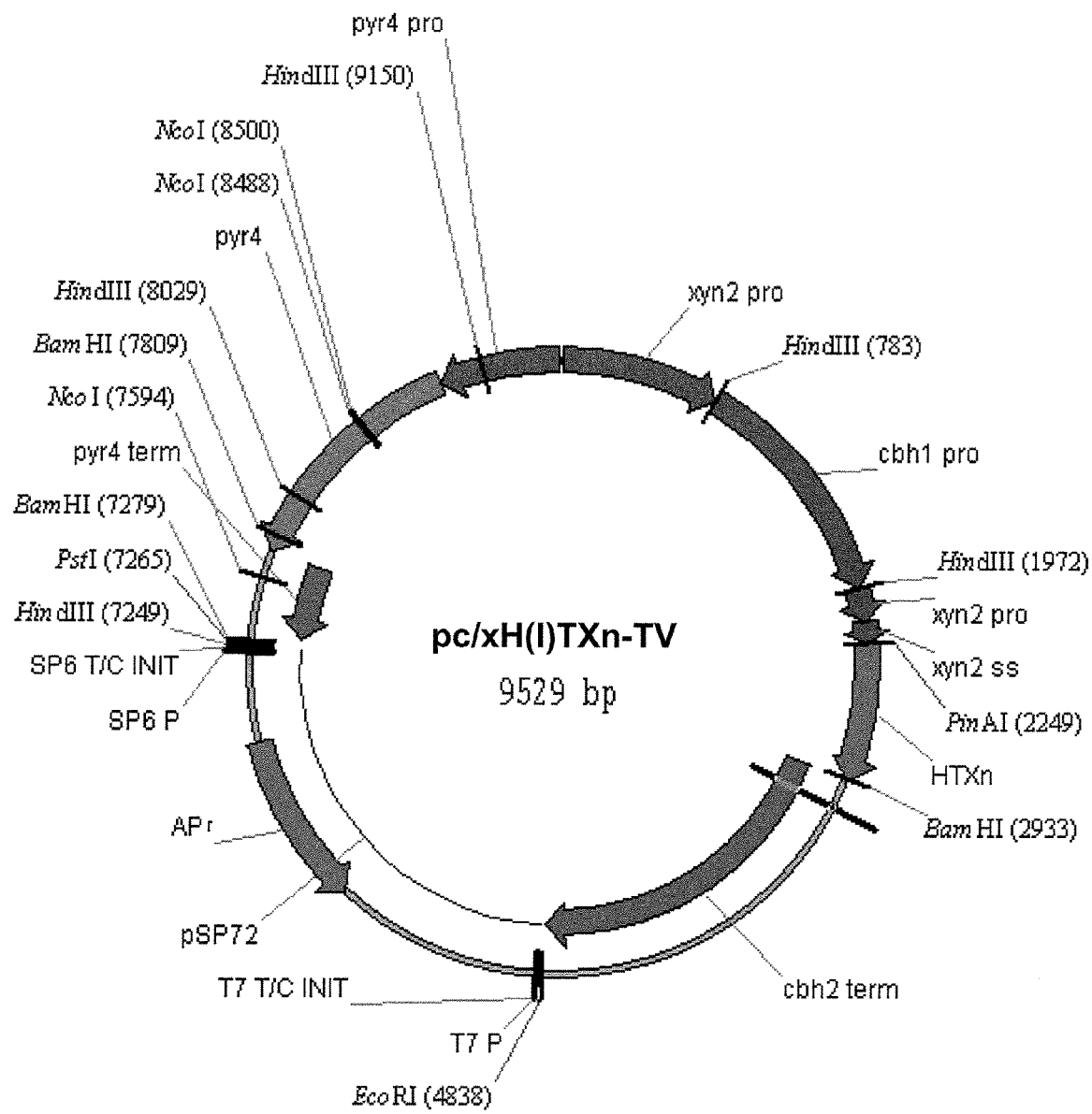
FIG. 4 shows a map of the general vector pc/xH(I)TXn-TV used to direct the expression of a modified xylanases in *T. reesei*, where "n" is the descriptor, for example "13", "18", "18(R135Y)", or "1(N131Q) and the vector may comprise a 131 N mutation (i.e., pc/xITXn-TV), or the vector may not comprise a 131N mutation (i.e., pc/xHTXn-TV). For example when "n" is 18, and the vector does comprise the 131N mutation, the vector is pc/XITXn-TV.

Each 3640 bp Sac I fragment containing the promoter regions, the modified xln2 genes and part of the cbh2 terminator from pALT-H(I)TXn (described in Example 4) was cloned into the Sac I site of a plasmid containing the remaining cbh2 terminator sequence in pSP72. This generates the expression cassette containing plasmids, pc/xH(I)TXnPSP. The selection cassette containing plasmid, pNCBglNSNB(r), was derived from a *N. crassa* pyr4 containing plasmid, pFB6 (Radford et al, 1985). A 3.2 kb Bgl II fragment from pFB6 containing the *N. crassa* pyr4 gene (GenBank accession M13448) as well as its promoter, terminator and some 5' UTR sequences was cloned into the Bam HI site of pUC119 modified to contain Not I, Sma I, Nhe I and Bgl II sites in the polylinker (between Eco RI and Sac I) to generate pNCBgl-NSNB(r). A 2238 bp Kpn I fragment containing the entire *N. crassa* pyr4 coding region, promoter and terminator sequences was isolated from pNCBgl-NSNB(r) and cloned into the unique Kpn I site of pc/xHTX18PSP to generate pc/xHTX18-TV (the plasmid is shown in its generic form "pc/xH(I)TXn-TV", in FIG. 4).

5.3 Construction of pc/xHTX18(R135Y)-TV

The 3640 bp Sac I fragment containing the promoter regions, the modified xln2 gene and part of the cbh2 terminator from pALT-HTX18(R135Y) was cloned into the Sac I site of a plasmid containing the remaining cbh2 terminator sequence in pSP72. This step generates the expression cassette containing plasmid pc/xHYX18(R135Y)PSP. The 2238 bp Kpn I fragment containing the entire *N. crassa* pyr4 coding region, promoter and terminator sequences was isolated from pNCBgl-NSNB(r) (described in Example 5.2, above) and cloned into the unique Kpn I site of the expression cassette-containing plasmids to generate pc/xHTX18(R135Y)-TV (the plasmid is shown in its generic form "pc/xH(I)TXn-TV", where "n" is "18(R135Y)" in FIG. 4).

5.4 Construction of pc/xxyn1-TV and pc/xxyn1-T118N-TV

The 675 bp wild type and modified xynI PCR products (described in example 3, above) were digested with NheI and BamHI and inserted into the corresponding sites in the plasmid pCB219N-N (described in example 5.1, above) to generate the plasmids pX1C2ter and pX1(118N)C2ter. An ~1.6 kb fragment comprising bp −1399 to −204 of the cbh1 promoter, bp −121 to −1 of the xln2 promoter and the sequence encoding the xln2 secretion signal was amplified from the plasmid pBR322LXC (described in example 5.1) using primers to introduce a XbaI site at bp −1399 of the cbh1 promoter and an NheI site directly downstream of the Gln codon comprising the first amino acid of the mature xylanase II protein. This PCR product was digested with XbaI and NheI and inserted upstream of the native and modified xylanase I coding regions in the corresponding sites of the plasmids pX1C2ter and pX1(118N)C2ter to generate the expression cassette plasmids pc/xxyn1-EC and pc/xxyn1-T118N-EC. The expression cassettes were excised by digestion with XbaI, blunting of the XbaI site with Klenow DNA polymerase and digestion with EcoRI. The *N. crassa* pyr4-containing plasmid pNCBglNSNB(r) (described in Example 5.2, above) was prepared to accept this fragment by digestion with NotI, blunting of the NotI site with Klenow DNA polymerase and digestion with EcoRI. The EcoRI-xyn1 expression cassette-XbaI° fragment was inserted between the EcoRI and NotI° sites downstream of the selection cassette to produce the transformation vectors pc/xxyn1-TV and pc/xxyn1-T118N-TV (FIG. 5). The final transformation vectors were linearized by digestion with XbaI prior to introduction into protoplasts of *T. reesei* M2C38aux5 via PEG-mediated transformation of protoplasts as described in Example 7.

5.5 Construction of pc/xxynC-T128N-TV

The xylanase I expression cassette plasmid, pc/xx1n1-EC, was digested with NheI and KpnI to drop-out the xylanase I coding region and the larger fragment was ligated with the 700 bp modified xynC PCR product (described in example 3, above) digested with NheI and KpnI to generate the expression cassette plasmid pc/xxynC-T128N-EC. The expression cassette was excised by digestion with NotI, blunting of NotI site with Klenow DNA polymerase and digestion with XbaI. At the same time, the hph-containing selection cassette plasmid pHPT136 (described in example 5.1, above) was prepared to accept this fragment by digestion with XhoI, blunting of the XhoI site with Klenow DNA polymerase and subsequent digestion with XbaI. The XbaI-xynC expression cassette-NotI° fragment was inserted between the XbaI and XhoI° sites upstream of the selection cassette of pHPT136. The final transformation vector, pc/xxynC-T128N-TV (FIG. 5), was linearized by digestion with XbaI prior to introduction into protoplasts *T. reesei* RutC30 via PEG-mediated transformation as described in Example 7.

Example 6

Isolation of a pyr4 Auxotroph of *Trichoderma reesei* Strain M2C38

In order to use the *N. crassa* pyr4 gene as a selectable marker, a spontaneous pyr4 auxotroph of M2C38 was isolated as follows: $1 \times 10^6$ spores of M2C38 were plated onto minimal media containing 5 mM uridine and 0.15% (w/v) of the uridine analog 5-fluoroorotic acid (FOA) as previously described for the selection of pyr4 auxotrophs of *T. reesei* (Berges and Barreau, 1991). The ability to grow on FOA-containing media will allow for selection of mutants disrupted in either the pyr2 gene encoding orotate phosphoribosyl transferase or the pyr4 gene encoding orotidine 5'-phosphate decarboxylase. Spontaneous FOA-resistant colonies were subjected to secondary selection of minimal media with and without uridine. Spores of FOA-resistant colonies that could not grow on minimal media were then transformed with pNCBglNSNB(r) (described in Example 5.2) by microprojectile bombardment and selected for growth on minimal media. Only those strains that were complemented by the *N. crassa* pyr4 gene in pNCBglNSNB(r) will grow on minimal media and are true pyr4 auxotrophs. Using these procedures, auxotroph 5 (M2C38aux5) was selected as a stable pyr4 auxotroph of M2C38.

Example 7

Transformation of the *Trichoderma reesei* M2C38

7.1 Transformation Via Microprojectile Bombardment

The Biolistic PDS-1000/He system (BioRad; E.I. DuPont de Nemours and Company) was used to transform spores of *T. reesei* strain M2C38 and all procedures were performed as recommended by the manufacturer. Gold particles (median diameter of 0.6 um, BioRad Cat. No. 1652262) were used as microcarriers. The following parameters were used in the optimization of the transformation: a rupture pressure of 1100 psi, a helium pressure of 29 mm Hg, a gap distance of 0.95 cm, a macrocarrier travel distance of 16 mm, and a target distance of 9 cm. Plates were prepared with $1 \times 10^6$ spores on miminal media agar (see example 7.2, below). Bombarded plates were incubated at 28° C. Transformants can be observed after 3-6 days growth at which time the colonies are transferred to MM agar in individual petri plates and allowed to grow and sporulate.

7.2 Protoplast Transformations Using Polyethylene Glycol(PEG) and $CaCl_2$ $5 \times 10^6$ spores of M2C38aux5 are plated onto sterile cellophane on Potato Dextrose agar supplemented with 5 mM uridine and are incubated for 20 hours at 30° C. to facilitate spore germination and mycelial growth. Cellophane discs with mycelia are transferred to 10 ml of a protoplasting solution containing 7.5 g/l Driselase and 4 g/l beta-glucanase (InterSpex Products Inc., Cat. Nos. 0465-1 and 0439-2, respectively) in 50 mM potassium phosphate buffer, pH 6.5 containing 0.6 M ammonium sulfate (Buffer P). The mycelial mat is digested for 5 hours at 28° C. with shaking at 60 rpm. Protoplasts are recovered by centrifugation at 1000-1500×g for 10 min at room temperature. Protoplasts are washed with 5 ml of Buffer P and centrifuged again at 1000-1500×g for 10 min at room temperature. Protoplasts are resuspended in 1 ml of STC buffer (1.2 M sorbitol, 10 mM $CaCl_2$, 10 mM Tris-HCL, pH 7.5) and separated from undigested mycelia by filtration through sterile No. 60 MIRACLOTH™ and collected into a sterile microcentrifuge tube.

For transformation, 0.1 ml of resuspended protoplasts (approximately $5 \times 10^6$ protoplasts) are combined with 2 µg vector DNA and 25 µl of PEG solution (25% PEG 4000, 50 mM $CaCl_2$, 10 mM Tris-HCl, pH 7.5). After incubation on ice for 30 min, 1 ml of PEG solution is added and the mixture incubated for 5 min at room temperature. Transformation mix is diluted with 2 ml of 1.2 M sorbitol in PEG solution and 0.75 ml of the mix is added to 25 mL of molten MMSS agar media (see below) cooled to about 47° C. and the protoplast suspension poured over MM agar (see below). Plates are incubated at 30° C. until colony growth is visible. Transformants are transferred to individual plates containing MM agar and allowed to sporulate. Spores are collected and plated at high dilution on MM agar to isolate homokaryon transformants, which are then plated onto PDA to allow for growth and sufficient sporulation to inoculate the screening cultures described in Example 9, below.

| Minimal medium (MM) agar contains: | |
|---|---|
| Reagent | Per L |
| $KH_2PO_4$ | 10 g |
| $(NH_4)_2SO_4$ | 6 g |
| $Na_3Citrate-2H_2O$ | 3 g |
| $FeSO_4—7H_2O$ | 5 mg |
| $MnSO_4—H_2O$ | 1.6 mg |
| $ZnSO_4—7H_2O$ | 1.4 mg |
| $CaCl_2—2H_2O$ | 2 mg |
| Agar | 20 g |
| 20% Glucose f.s. | 50 ml |
| 1 M $MgSO4—7H_2O$ f.s. | 4 mL | pH to 5.5

MMSS agar contains the same components as MM agar plus 1.2 M sorbitol, 4 mM $MgSO_4$, 1 g/L YNB (Yeast Nitrogen Base w/o Amino Acids from DIFCO Cat. No. 291940) and 0.12 g/l amino acids (-Ura DO Supplement from CLONTECH Cat. No. 8601-1).

Example 8

Detection of Xylanase Activity in *T. reesei* Culture Filtrates

Detection of Thermophilic Xylanase Activity Due to Expression of HTX18, HTX18(R1351), ITX1-5, and ITX3'-5

The presence of thermophilic xylanase activity in culture filtrates of *T. reesei* transformants is determined by measuring the release of reducing sugars from a soluble arabinoxylan substrate at 65° C. Specifically, 30 µl of an appropriate dilution of culture filtrate is pre-incubated at 65° C. for 5 min. Subsequently, 300 µl of a solution of 1.5% wheat arabinoxylan (Megazyme International) redissolved in pH 7.0 phosphate buffer containing 0.04% Tween, also pre-incubated at 65° C. for 5 min, is added to the enzyme sample in a microcentrifuge tube. The tubes are vortexed briefly to facilitate mixing and then the reaction is incubated at 65° C. for 20 min. The enzymatic hydrolysis reaction is stopped by the addition of 150 µl of the stopping solution containing 43.64 mM 2-hydroxy-3,5-dinitrobenzoic acid, 0.93M sodium potassium tartrate, 0.4M sodium hydroxide and 0.4 M potassium hydroxide. The resulting solution is then boiled for 10 minutes to facilitate reaction of the 2-hydroxy-3,5-dinitrobenzoic acid with the reducing sugars released from the arabinoxylan substrate by the enzyme. The tubes are cooled in a cold water bath for 5 minutes and then 1.5 ml of deionized water is added. The absorbance of the solution is measured at 530 nm. The amount of reducing sugar released by the thermophilic xylanases during the incubation is calculated from a standard curve of A530 measurements of several dilutions of a pure xylose solution reacted with the same stopping solution.

Detection of Xylanase I Activity Due to Overexpression of Native or Modified *T. reesei* Xylanase I and *S. lividans* Xylanase C-131N Detection of xylanase I activity in culture filtrates of *T. reesei* strains overexpressing the native or modified xylanase I was carried out as described in Section 8.1, above, except that the incubations were carried out at 40° C. and the 1.5% wheat arabinoxylan substrate was prepared in acetate buffer at pH 4.0 containing 0.04% Tween.

Detection of xylc-131N activity in culture filtrates of *T. reesei* strains overexpressing the modified *S. lividans* xylanase C was carried out as described in Section 8.1, above, except that the incubations were carried out at 40° C. and the 1.5% wheat arabinoxylan substrate was prepared in acetate buffer at pH 6.0.

Example 9

Production of Modified Xylanases in Liquid Cultures

Individual colonies of *Trichoderma* are transferred to PDA plates for the propagation of each culture. Sporulation is necessary for the uniform inoculation of shake flasks which are used in testing the ability of the culture to produce the thermophilic xylanases and cellulase. The culture media is composed of the following:

| Component | g/L |
|---|---|
| $(NH_4)_2SO_4$ | 6.35 |
| $KH_2PO_4$ | 4.00 |
| $MgSO_4$—$7H_2O$ | 2.02 |
| $CaCl_2$—$2H_2O$ | 0.53 |
| CSL | 6.25 |
| $CaCO_3$ | 10.00 |
| Carbon source** | 5-200 |
| Trace elements* | 1 mL/L |

*Trace elements solution contains 5 g/l $FeSO_4*7H_2O$; 1.6 g/l $MnSO_4*H_2O$; 1.4 g/l $ZnSO_4*7H_2O$.
**glucose, Solka floc, lactose, cellobiose, sophorose, corn syrup, or Avicel. The carbon source can be sterilized separately as an aqueous solution at pH 2 to 7 and added to the remaining media initially or through the course of the fermentation.

Individual transformants are grown in the above media in 150 mL cultures in 1-litre flasks or in 1 mL cultures in 24-well microplates. The initial pH is 5.5 and the media sterilized by steam autoclave for 30 minutes at 121° C. prior to inoculation. For both native and transformed cells, spores are isolated from the PDA plates as described in Example 8 and $10^4$-$10^6$ spores per ml are used to inoculate each culture. The cultures are shaken at 200-300 rpm at a temperature of 28° C. for a period of 6 days. The biomass is separated from the filtrate containing the secreted protein by filtration through GF/A glass microfibre filters (Whatman) or by centrifugation at 12000 rpm. The protein concentration is determined using the Bio-Rad Protein Assay (Cat. No. 500-0001). Xylanase activity is determined as described in Example 8. Strains expressing the highest xylanase activity from each construct and exhibiting high overall protein production were selected for growth in 14-litre pilot fermentations.

Example 10

Production of Xylanases in 14L Fed-Batch Fermentations

*T. reesei* strains were grown on Potato Dextrose Agar at 28-30° C. until a confluent lawn of spores was obtained. Spores were collected and used to inoculate 750 ml of Berkeley media (10 g/l glucose, 1.4 g/l $(NH_4)_2SO_4$, 2.0 g/l $KH_2PO_4$, 0.31 g/l $MgSO_4*7H_2O$, 0.53 g/l $CaCl_2$; 5.1 g/l dry corn steep, 5 mg/l $FeSO_4*7H_2O$; 0.8 mg/l $MnSO_4*H_2O$, 0.7 mg/l $ZnSO_4*7H_2O$) in a 2 L baffled flask. After 3 days of growth at 28° C. and 150 rpm, this culture was used to inoculate 10 L of fermentation medium with the following initial composition: 13 g/l glucose, 2.2 g/l $(NH_4)_2SO_4$, 1.39 g/l $KH_2PO_4*7$ g/l $MgSO_4*7H_2O$, 0.185 g/l $CaCl_2$, 6 g/l dry corn steep, 3.75 mg/l $FeSO_4*7H_2O$; 1.2 mg/l $MnSO_4*H_2O$, 1.05 g/l $ZnSO_4*7H_2O$. A fed-batch aerobic fermentation using one or more of the inducing carbohydrate sources listed in Example 9 is run for 6 days at pH 4.5 and 28-30° C. in a 14L New Brunswick Microferm fermentor. After 6 days, the culture is filtered over Harborlite and the culture filtrate adjusted to pH 4.5 and preserved with 0.5% benzoate to prevent microbial growth.

Expression of the modified xylanases did not significantly alter the growth of the *Trichoderma* host strains, as all fermentations accumulated similar amounts biomass by the end of 6 days of growth (Table 3). Biomass concentration in fermentor samples was determined as follows: 5-10 g of fermentation broth is weighed and recorded. The fermentation broth is then filtered over a pre-weighed glass micro-fiber filter paper (Whatman) and washed with water. The filtered biomass is dried overnight in a 100° C. oven. The weight of the dried biomass is determined by subtracting the mass of the filter paper from the mass of the dried biomass plus filter paper. The biomass is calculated as follows:

$$\text{Biomass}(g/L) = \frac{\text{Mass of dry biomass}(g)}{\text{Mass of wet biomass}(g)} \times \text{Density of sample}(g/mL) \times \frac{1000\ mL}{L}$$

Strains producing the modified xylanases comprising any of the X34N, X131N, X180N or X182N mutations (see Table 2 for description of mutations) produced higher levels of total protein than strains producing the corresponding unmodified xylanases (Table 3). The protein concentration in daily fermentor samples was determined using the Bio-Rad Protein Assay (Cat. No. 500-0001).

produce up to two-fold higher xylanase activity than strain P67AB expressing the unmodified HTX18.

Strains P322B and P323B, comprising modified xylanase genetic constructs containing the N-glycosylation motif N-X-S/T at positions 182-184 of the *T. reesei* xylanase II sequence in addition to the mutations present in HTX18, produce up to 3.5-fold higher xylanase activity than strain P67AB expressing the unmodified HTX18.

Strains P331B and P336B, comprising modified xylanase genetic constructs containing the N-glycosylation motif N-X-S/T at positions 34-36 of the *T. reesei* xylanase 11 sequence in addition to the mutations present in HTX18, produce 1.6- and 2.1-fold higher xylanase activity than strain P67AB expressing the unmodified HTX18, respectively.

Strain P279A, comprising a modified xylanase genetic construct containing the N-glycosylation motif N-X-T at positions 118-120 of the native *T. reesei* xylanase I sequence, produces 15.0 times higher xylanase activity than strain P300A expressing the unmodified xylanase I. This mutation is equivalent to X131N of *T. reesei* xylanase II (see FIG. 1).

TABLE 3

Expression of modified xylanases from transformed *T. reesei* strains (biomass and xylanase activity).

| Strain | Enzyme | New N—X—S/T site | Protein (mg/ml) | Biomass (g/l) | Xylanase Activity (XU/ml) | increase in expression fold × (% increase)[b] |
|---|---|---|---|---|---|---|
| RutC30 | Native xylanase | — | 40.89 | 30.35 | 812.5[c] | — |
| M2C38 | Native xylanase | — | 23.93 | 18.11 | 141[a] | — |
| P67AB | HTX18 | None | 18.9 | 20.1 | 3302 | — |
| 2013B | HTX18-R135Y | None | 34.9 | 24.0 | 6166 | 1.86 × (86%) |
| P210A | ITX1 (T131N, R135Y) | 131N | 44.7 | 26.5 | 15288 | 4.6 × (360%)[c] 2.5 × (150%)[d] |
| P284A | ITX2 | 131N | 42.9 | 21.3 | 9691 | 2.9 × (190%) |
| P304B | ITX3 | 180N | 43.2 | 20.5 | 6546 | 2.0 (100%)× |
| P321H | ITX3' | 180N/182T | 40.5 | 22.8 | 7192 | 2.2 × (120%) |
| P322B | ITX4 | 182N | 39.0 | 20.2 | 11083 | 3.4 × (240%) |
| P323B | ITX4' | 182N/184T | 33.0 | 19.2 | 12061 | 3.6 × (260%) |
| P331B | ITX5 | 34N | 34.5 | 22.5 | 5275 | 1.6 × (60%) |
| P336B | ITX5' | 34N/36T | 38.0 | 22.6 | 6933 | 2.1 × (110% |
| P300A | Xyn 1 | No | 31.0 | 23.2 | 136[a] | — |
| P279A | Xyn 1-131N | 118N | 31.75 | 25.5 | 2042[a] | 15.0 × (1400%) |
| P348C | xlnC-131N | 128N | 35.2 | 23.8 | 2365[e] | ND |

[a]measured at 40° C., pH 4.0
[b]relative to the expression of the corresponding unmodified xylanase comprising the same primary amino acid sequence except for the newly introduced glycosylation motif
[c]xylanase expression efficiency relative to P67AB expressing a modified xylanase comprising Y135R mutation but without 131N
[d]xylanase expression efficiency relative to strain 2013B expressing a modified xylanase comprising neither the T131N nor the Y135R mutation.
[e]measured at 40° C., pH 6.0

Xylanase activity was determined as described in Example 8.

Strains P210A and P284A, comprising modified xylanase genetic constructs containing the N-glycosylation motif N-X-T at positions 131-133 of the *T. reesei* xylanase II sequence in addition to the mutations present in HTX18, produce 4.6- and 2.9 fold higher xylanase activity than the HTX18 production strain, P67AB, respectively.

Strains P304B and P321H, comprising modified xylanase genetic constructs containing the N-glycosylation motif N-X-S/T at positions 180-182 of the *T. reesei* xylanase II sequence in addition to the mutations present in HTX18, Strain P348C, comprising a modified xylanase genetic construct containing the N-glycosylation motif N-X-T at positions 128-130 of the native *S. lividans* xylanase C sequences produces similarly high levels of xylanase activity as strain P279A, comprising a modified xylanase genetic construct containing the N-glycosylation motif N-X-T at positions 118-120 of the native xylanase I sequence, which is commercially significant for the manufacturing of xylanase for industrial applications. This mutation is equivalent to X131N of *T. reesei* xylanase II (see FIG. 1).

Strains P321H, P323B and P336B, comprising modified xylanase genetic constructs containing N-X-T glycosylation motifs produce higher amounts of xylanase activity than strains P304B, P322B and P331B, comprising modified xylanase genetic constructs containing N-X-S glycosylation motifs in the same respective positions within the xylanase II sequence.

Example 11

Comparison of the Alkalophilicity and Thermophilicity of the Modified Xylanase ITX1 with its Native Counterpart HTX18

Activity measurements were determined as described in Example 8. To determine alkalophilicity (FIG. 6), the incubation temperature of the assay was reduced to 55° C. and the phosphate buffer containing Tween-20 and the NSP substrate solutions were adjusted to the desired pH for activity measurements. To determine thermophilicity (FIG. 7), the incubation temperature was adjusted to the desired temperature for activity measurements.

Figure 7:
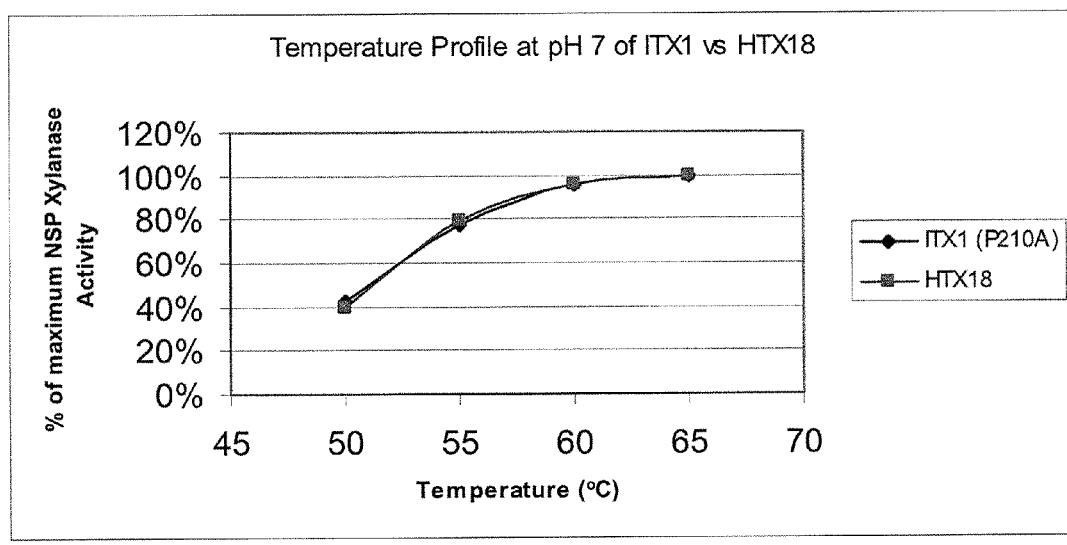
FIG. 7 shows the temperature activity profile for the modified xylanase ITX1 and its native counterpart HTX18.

The modified ITX1 xylanase produced by strain P210A, comprising the same mutations as HTX18 but without the Y135R mutation and the T131N mutation (see Table 2), has a similar pH and temperature activity profile as the HTX18 xylanase (FIGS. 6 and 7). Thus the addition of the T131N mutation does not alter the desirable biophysical and biochemical properties of the xylanase due to the other mutations. This is significant for the utility of increasing the expression of any target Family 11 from *Trichoderma* via the introduction of the X131N mutation (TrX numbering).

The gel bands were allowed to re-swell for 10 minutes and were topped off with approximately 30 mL of 50 mM ammonium bicarbonate (enough to ensure that the gel pieces were completely submerged during the digestion). The digestion was allowed to continue for 4 hours after which the liquid from each sample was transferred to a fresh vial. The solutions were evaporated on a Savant to a final volume of approximately 10 mL.

The digestion solutions were analyzed by nanoHPLC-tandem mass spectrometry (nanoLC-MS/MS) using a CapLC system (Waters) coupled with a Q-TOF2 hybrid quadrupole time-of-flight mass spectrometer (Waters). 3 mL of the 10 mL digests were injected onto a 0.3×5 mm C18 micro precolumn cartridge (Dionex/LC Packings). The peptides were retained while the salts and other solution components were washed away. The trap was then brought on-line with a 75 mm×150 mm C18 nano-Series column (Dionex/LC-Packings) and the peptides were separated by gradient elution (3-45% acetonitrile, 0.2% formic acid in 35 minutes followed by a rapid increase to 85% at 38.5 minutes). The mass spectrometer was set to acquire MS/MS spectra in automated mode for doubly and triply charged ions. Priority was given to multiply charged ions from the tryptic peptide 123-141 with and without a HexNAc residue attached. The MS/MS spectra were analyzed manually.

TABLE 4

| | Detection of glycosylation at 131N by LC-MS/MS | | | |
|---|---|---|---|---|
| Peptide | LC retention time | M/z of doubly-charged ion | Amino Acid sequence | Distribution |
| aa 123-141 | 25.4 min | 1203.5367 | VNAPSIEGN * ATFYQYWSVR + N-acetyl hexosamine | ~80% |
| aa 123-141 | 26.7 min | 1102.009 | VNAPSIEGNATFYQYWSVR | ~20% |

Example 12

Mass-Spectral Analysis of the ITX1 Enzyme Comprising the T131N Mutation

The fermentation filtrate produced by strain P210A and containing the modified xylanase ITX1 were diluted in 2× Laemmli buffer (62.5 mM Tris-HCl pH 6.8, 10% glycerol, 2% SDS, 5% β-mercaptoethanol), boiled for 5 min and cooled. The proteins were separated by SDS-PAGE using a resolving gel containing 12% acrylamide (37.5:1 acrylamide: bisacrylamide, BioRad Cat. No. 161-0122) using a Mini-PROTEAN® 3 Electrophoresis Cell (BioRad Cat. No. 165-3301) running at 200V (constant) for 40 min. The proteins in the gel were visualized with staining using Bio-Safe™ Coomassie Stain (BioRad Cat. No. 161-0786). The protein band at 20 kDa was excised from the gel, destained and in-gel digested with trypsin as per standard protocols. Briefly, the gel bands were rinsed with 30% acetonitrile in 100 mM ammonium bicarbonate for approximately 10 minutes and the supernatant was discarded. This procedure was repeated until the stain was completely removed. The gel bands were then washed with deionized water and followed by acetonitrile. Approximately, 20 mL of 50 mM ammomium bicarbonate containing 200 ng of trypsin was added to each gel band.

These results confirm that the *Trichoderma* host strain recognizes the NAT consensus N-glycosylation motif introduced via mutation of T131N and that the introduction of this functional glycosylation motif facilitates high level expression of the modified xylanase from *Trichoderma*.

In summary, modified xylanase demonstrating increased expression efficiency from *Trichoderma* can be constructed through mutation of X131N (TrX numbering). A similar increase in expression efficiency may also be obtained by introducing other N-X-S/T N-glycosylation motifs into a Family 11 xylanase at positions X34N, X180N, X182N, X34N-S36T, X180N-S182T, X182N-S184T, or a combination thereof, at equivalent positions when the Family 11 xylanase is aligned with TrxII, as described herein.

The present invention has described mutant xylanases that exhibit increased expression and secretion from a *Trichoderma* host. These mutant xylanases may be used in industrial processes such as pulp and paper processing, as animal feed additives, or in baking and brewing applications.

The present invention has been described with regard to one or more embodiments. However, it will be apparent to persons skilled in the art that a number of variations and modifications can be made without departing from the scope of the invention as defined in the claims.

All references and citations are herein incorporated by reference.

REFERENCES

Arase, A., Yomo, T., Urabe, I., Hata, Y., Katsube, Y. and Okada, H. (1993) FEBS Lett. 316:123-127.

Berka, R. M., Kodama, K. H., Rey, M. W., Wison, L. J. and Ward, M. (1991) The development of *Aspergillus niger* var. *awarmori* as a host for the expression and secretion of heterologous gene products. Biochem. Soc. Trans. 19: 681-685.

Berges, T. and Barreau, C. (1991) Isolation of uridine auxotrophs from *Trichoderma reesei* and efficient transformation with the cloned ura3 and ura5 genes. Curr. Genet. 19: 359-365.

Bissett, J. (1984) A revision of the genus *Trichoderma* 1. Section Longibrachiatum Sect. nov. Can. J. Bot. 62: 924-931.

Campbell, R. L., Rose, D. R., Sung, W. L., Yaguchi, M. and Wakarchuk, W. (1995) U.S. Pat. No. 5,405,769 issued on Apr. 11, 1995.

Cannon, P. (1986) International Commission on the Taxonomy of Fungi (ICTF): name changes in fungi of microbiological, industrial and medical importance, Part 2, Microb. Sci, Vol. 3

Chen, C. M., Gritzali, M. and Stafford, D. W. (1987) "Nucleotide sequence and deduced primary structure of cellobiohydrolase II from *Trichoderma reesei*", Bio/Technology 5: 274-278

Conesa, A., Punt, P. J., van Luijk, N. and van den Hondel, C. A. M. J. J. (2001) The secretion pathway in filamentous fungi: a biotechnological view. Fung. Genet. Biol. 33: 155-171.

Goldman, VanMontagu and Herrera-Estrella, (1990) "Transformation of *Trichoderma harzianum* by high-voltage electric pulse", Curr. Genet. 17:169-174

Gritz, L. and Davies, J. (1983) Plasmid-encoded hygromycin B resistance: the sequence of hygromycin B phosphotransferase gene and its expression in *Escherichia coli* and *Saccharomyces cerevisiae*. Gene 25: 179-188

Henrissat, B. (1991) A classification of glycosyl hydrolases based on amino acid sequence similarities. Biochem. J. 280: 309-316.

Hui, J. P. M., Lanthier, P., White, T. C., McHugh, S. G., Yaguchi, M., Roy, R., and Thibault, P. (2001) Characterization of cellobiohydrolase I (cel7a) glycoforms from extracts of *Trichoderma reesei* using capilliary isoelectric focusing and electrospray mass spectrometry. J. Chrom. B. 752: 349-368.

Hui, J. P. M., White, T. C, and Thibault, P. (2002) Identification of glycan structure and glycosylation sites in cellobiohydrolase II and endoglucanases I and II from *Trichoderma reesei*. Glycobiology 12: 837-849.

Kuhis, K., Lieckfeldt, E., Samuels, G. J., Kovacs, W. Meyer, W., Petrini, O. Gams, W. Börner, T. & Kubicek, C. P. (1996) Molecular evidence that the asexual industrial fungus *Trichoderma reesei* is a clonal derivative of the ascomycete *Hypocrea jecorina*. Proc. Natl. Acad. Sci. 93: 7755-7760.

Kulkarni, N., Shendye, A. and Rao, M. (1999) Molecular and biotechnical aspects of xylanases. FEMS Microbiol. Rev. 23: 411-456

Lorito, Hayes, DiPietro and Harman, 1993, Biolistic Transformation of *Trichoderma harzianum* and *Gliocladium virens* using plasmid and genomic DNA. Curr. Genet. 24: 349-356.

Lüithi, E., Jasmat, N. B., and Bergquist, P. L. (1990) Appl. Environ. Microbiol. 56:2677-2683.

Mandels, M. and Reese, E. T. (1957) Induction of cellulase in *Trichoderma viride* as influenced by carbon sources and metals. J. Bacteriol. 73: 269-278.

Mantyla, A., Paloheimo, M., Lantto, R., Fagerstrom, R., Lahtinen, T., Suominen, P., and Vehmaanpera, J. (2003) Sequences of Xylanase and Xylanase Expression Vectors. U.S. Pat. No. 6,667,170.

Montenecourt, B. and Eveleigh, D. (1979) Selective isolation of high yielding cellulase mutants of *T. reesei*. Adv. Chem. Ser. 181: 289-301.

Paloheimo, M., Mantyla, A., Kaooio, J. and Suominen, P. (2003) High-yield production of a bacterial xylanase in the filamentous fungus *Trichoderma reesei* requires a carrier polypeptide with an intact domain structure. Appl. Environ. Microbiol. 69: 7073-7082.

Paloheimo, M., Hakola, S., Mantyla, A., Vehmaanpera, J., Lantto, R., Lahtinen, T., Fagerstrom, R. B., and Suominen, P. (2001) Xylanases, genes encoding them, and uses thereof. U.S. Pat. No. 6,635,464.

Penttila, Nevalainen, Ratto, Salminen and Knowles (1987) A versatile transformation system for the cellulolytic fungus *Trichoderma reesei*. Gene 6:155-164.

Radford, A., Buston, F. P., Newbury, S. F. and Glazebrook, J. A. (1985) Regulation of pyrimidine metabolism in *Neurospora*. In Molecular Genetics of Filamentous Fungi (Timberlake, W. E., editor), Alan R. Liss (New York), pages 127-143.

Saarelainen, R., Paloheimo, M., Fagerstrom, R., Suominen, P. L., and Nevalainen, K. M. H. (1993) Cloning, sequencing and enhanced expression of the *Trichoderma reesei* endoxylanase II (pI 9), xln2. Mol. Gen. Genet. 241: 497-503.

Sagt, C. M. J., Kleizen, B., Verwaal, R., deJong, M. D. M., Müller, W. H., Smits, A., Visser, C., Boonstra, J., Verkleij, A. J. and Verrips, C. T. (2000) Introduction of an N-glycosylation site increases secretion of heterologous proteins in yeasts. Appl. Environ. Microbiol. 66 (11): 4940-4944.

Saloheimo, M., Lund, M. and Penttila, M. (1999) The protein disulphide isomerase gene of the fungus *Trichoderma reesei* is induced by endoplasmic reticulum stress and regulated by the carbon source. Mol. Gen. Genet. 262: 35-45.

Sambrook, Fritsch and Maniatis (1989) Molecular Cloning: A Laboratory Manual, Second Edition, Cold Spring Harbor Press.

Shoemaker, Schweikart, Ladner, Gelfand, Kwok, Myambo and Innis (1983) Molecular cloning of exo-cellobiohydrolyase 1 derived from *Trichoderma reesei* strain L27. Bio/Technology 1: 691-696.

Simmons, E. G. (1977) Classification of some cellulase-producing *Trichoderma* species. In: Bigelow, H. And Simmons, E. (Eds.), Second International Mycological Congress, Abstracts, Vol. 2, University of South Florida, Tampa, Fla., 618.

Simpson, H. D., Haufler, U. R., and Daniel, R. M. (1991) Biochem. J. 277: 413-417.

Sung, W. L., Luk, C. K., Zahab, D. M. and Wakarchuk, W. (1993) Protein Expression Purif. 4: 200-206.

Sung, W. L., Yaguchi, M. and Ishikawa, K. (1998) U.S. Pat. No. 5,759,840, issued on Jun. 2, 1998.

Sung, W. L., Yaguchi, M. and Ishikawa, K. (1999) U.S. Pat. No. 5,866,408, issued on Feb. 2, 1999

Tsai, B., Ye, Y. and Rapoport, T. A. (2002). Retro-translocation of proteins from the endoplasmic reticulum into the cytosol. Nature Reviews-Molecular Cell biology 3: 246-255

Te'o, V. S. J., Cziferszky, A. E., Bergquist, P. L., and Nevalainen, K. M. H. (2000) Codon optimization of xylanase gene xynB from the thermophilic bacterium *Dictyoglomus thermophilum* for expression in the filamentous fungus *Trichoderma reesei*. FEMS Microbiol. Letters 190: 13-19.

Törrönen, A., Mach, R. L., Messner, R., Gonzalez, R., Kalkkinen, N., Harkki, A., and Kubicek, C. P. (1992) The two major xylanases from *Trichoderma reesei*: characterization fo both enzymes and genes. Bio/technology 10:1461-1465.

Turenen, O., Etuaho, K., Fenel, F., Vehmaanpera, J., Wu, X. Rouvinen, J., and Leisola, M. (2001) J. Biotech. 88:37-46.

van den Brink, H., Andreasen, B., Rahbek-Nielsen, H., Hellmuth, K., and Harboe, M. (2004) Glycosylation as a tool for improved protein production in *Aspergillus niger*. Abstract for poster VIII p-21, 7th European Conference on Fungal Genetics, Copenhagen (Apr. 17-20, 2004).

van den Elzen, P. J. M., Townsend, J., Lee, K. Y., Bedbrook, J. R. (1985) A chimaeric hygromycin resistance gene as a selectable marker in plant cells. Plant Mol. Biol. 5: 299-302.

Vanhanen, Penttila, Lehtovaara and Knowles (1989) Isolation and characterization of the 3-phosphoglycerate kinase gene (pgk) from the filamentous fungus *Trichoderma reesei*. Curr. Genet. 15: 181-186, 1989.

Vanhanen, Saloheimo, Ilmen, Knowles and Penttila (1991) Promoter structure and expression of the 3-phosphoglycerate kinase gene (pgk1) of *Trichoderma reesei*. Gene 106: 129-133.

Viera and Messing (1987) Isolation of single-stranded plasmid DNA. Methods Enzymol. 153: 3.

Winterhalter C. and Liebl, W. (1995) Appl. Environ. Bicrobiol. 61: 1810-1815.

The embodiments of the invention in which an exclusive property of privilege is claimed are defined as follows:

1. A method for increasing the expression efficiency of a Family 11 xylanase from a *Trichoderma* host comprising:
   (a) introducing a functional consensus N-glycosylation site into a Family 11 xylanase coding region that is not found in a parental Family 11 xylanase coding region by substitution of the native amino acid at one or more of positions 34, 131, 180 and 182 with an asparagine, the position being determined by alignment of the Family 11 xylanase with the amino acid sequence of SEQ ID NO: 1, to produce a modified Family 11 xylanase coding region;
   (b) incorporating a DNA encoding the modified Family 11 xylanase coding region produced in step (a) into a genetic construct comprising a promoter and a secretion signal sequence operatively linked to said modified Family 11 xylanase coding region;
   (c) transforming a *Trichoderma* host microbe with the genetic construct of step (b) and selecting for genetically modified *Trichoderma* expressing the modified Family 11 xylanase; and
   (d) culturing the genetically modified *Trichoderma* of step (c) in suitable medium to induce expression and secretion of the modified Family 11 xylanase
   wherein the expression efficiency of the modified Family 11 xylanase is at least 40% higher than that of a parental Family 11 xylanase when expressed using the same method.

2. The method of claim 1, wherein the *Trichoderma* host microbe is a member of the genus *Trichoderma* or *Hypocrea*.

3. The method of claim 1, wherein the *Trichoderma* host microbe is *Trichoderma reesei*.

4. The method of claim 1, wherein the secretion signal is a *Trichoderma* secretion signal.

5. The method of claim 4, wherein the *Trichoderma* secretion signal is a xylanase secretion signal.

6. The method of claim 5, wherein the xylanase secretion signal is a *Trichoderma* xylanase I secretion signal or a *Trichoderma* xylanase II secretion signal.

7. The method of claim 1, wherein the promoter is selected from the group consisting of a *Trichoderma* cbh1 promoter, a cbh2 promoter, an eg1 promoter, an eg2 promoter, an eg3 promoter, an eg5 promoter, a xln1 promoter, a xln2 promoter, and a combination of at least two of these promoters.

8. The method of claim 1, wherein the modified Family 11 xylanase coding region has the amino acid sequence of SEQ ID NO: 1 with the following amino acid substitutions:

N10H, Y27M, N29L, S75A, L105H, S125A, I129E, T131N, H144R, N157D, Q161R, Q162H and T165R;

N10H, Y27M, N29L, S75A, L105H, S125A, I129E, T131N, Y135R, H144R, N157D, Q161R, Q162H and T165R;

N10H, Y27M, N29L, S75A, L105H, S125A, I129E, H144R, N157D, Q161R, Q162H, T165R and F180N;

N10H, Y27M, N29L, S75A, L105H, S125A, I129E, H144R, N157D, Q161R, Q162H, T165R, F180N and S182T;

N10H, Y27M, N29L, S75A, L105H, S125A, I129E, H144R, N157D, Q161R, Q162H, T165R and S182N;

N10H, Y27M, N29L, S75A, L105H, S125A, I129E, H144R, N157D, Q161R, Q162H, T165R, S182N and S184T;

N10H, Y27M, N29L, Q34N, S75A, L105H, S125A, I129E, H144R, N157D, Q161R, Q162H and T165R; and N10H, Y27M, N29L, Q34N, S36T, S75A, L105H, S125A, I129E, H144R, N157D, Q161R, Q162H and T165R.

9. The method of claim 1, wherein the modified Family 11 coding region is *Trichoderma reesei* xylanase I with a substitution of threonine at position 118 with asparagine.

10. The method of claim 1, wherein the modified Family 11 coding region is *Streptomyces lividans* xylanase C with a substitution of threonine at position 128 with asparagine.

11. The method of claim 1, wherein the modified Family 11 coding region comprises X34N.

12. The method of claim 1, wherein the modified Family 11 coding region comprises X131N.

13. The method of claim 1, wherein the modified Family 11 coding region comprises X180N.

14. The method of claim 1, wherein the modified Family 11 coding region comprises X182N.

* * * * *

UNITED STATES PATENT AND TRADEMARK OFFICE
CERTIFICATE OF CORRECTION

| | |
|---|---|
| PATENT NO. | : 7,691,609 B2 |
| APPLICATION NO. | : 12/266666 |
| DATED | : April 6, 2010 |
| INVENTOR(S) | : Theresa C. White et al. |

It is certified that error appears in the above-identified patent and that said Letters Patent is hereby corrected as shown below:

ON TITLE PAGE 2 COLUMN 2 AT (56) OTHER PUBLICATIONS

Under "Simpson, et al.,": "termophiulic" should read --thermophilic--.

COLUMN 4

Line 22, "Family 111" should read --Family 11--; and
Line 52, "xylanases" should read --xylanase--.

COLUMN 5

Line 49, "indicates that the amino acid "X" at" should read
--"X" indicates that the amino acid at--

COLUMN 9

Line 39, "there between," should read --therebetween,--;
Line 48, "there between," should read --therebetween,--; and
Line 61, "it" should be deleted.

COLUMN 12

Line 55, "least," should read --least--; and
Line 66, "there between," should read --therebetween,--.

COLUMN 14

Line 67, "strains" should read --strains RutC30--.

COLUMN 18

Line 24, "B and Prep" should read --BandPrep--.

Signed and Sealed this

Thirteenth Day of July, 2010

David J. Kappos
*Director of the United States Patent and Trademark Office*

CERTIFICATE OF CORRECTION (continued)
U.S. Pat. No. 7,691,609 B2

COLUMN 22

Line 2, "analysis" should read --analysis.--;
    Line 29, "SphI and SalI" should read --Sph1 and Sal1--;
    Line 30, "EcoRI and SalI" should read --EcoR1 and Sal1--;
    Line 54, "EcoRI" should read --EcoR1--;
    Line 55, "EcoRI-" should read --EcoR1- --;
    Line 56, "NotI" should read --Not1--;
    Line 57, "EcoRI" should read --EcoR1--.
    Line 66, "SphI" should read --Sph1--; and
    Line 67, "KpnI" should read --Kpn1--.

COLUMN 23

Line 2, "SphI" should read --Sph1--;
    Line 3, "KpnI" should read --Kpn1--;
    Line 22, "KpnI" should read --Kpn1--;
    Line 26, "KpnI" should read --Kpn1--;
    Line 27, "KpnI" should read --Kpn1--;
    Line 29, "KpnI" should read --Kpn1--;
    Line 33, "KpnI" should read --Kpn1--;
    Line 37, "KpnI" should read --Kpn1--; and
    Line 38, "KpnI" should read --Kpn1--.

COLUMN 27

Line 50, "xylc-131N" should read --xylC-131N--.

COLUMN 28

Line 54, "*7 g/l $MgSO_4$" should read --0.7 g/l $MgSO_4$--.

COLUMN 35

Line 13, "fo" should read --of--.

COLUMN 70

Line 46, "xylanase" should read --xylanase,--.

SEQUENCE LISTING

```
<160> NUMBER OF SEQ ID NOS: 48

<210> SEQ ID NO 1
<211> LENGTH: 190
<212> TYPE: PRT
<213> ORGANISM: Trichoderma reesei

<400> SEQUENCE: 1

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 2
<211> LENGTH: 178
<212> TYPE: PRT
<213> ORGANISM: Trichoderma reesei
```

-continued

```
<400> SEQUENCE: 2

Ala Ser Ile Asn Tyr Asp Gln Asn Tyr Gln Thr Gly Gly Gln Val Ser
 1               5                  10                  15

Tyr Ser Pro Ser Asn Thr Gly Phe Ser Val Asn Trp Asn Thr Gln Asp
                20                  25                  30

Asp Phe Val Val Gly Val Gly Trp Thr Thr Gly Ser Ser Ala Pro Ile
             35                  40                  45

Asn Phe Gly Gly Ser Phe Ser Val Asn Ser Gly Thr Gly Leu Leu Ser
     50                  55                  60

Val Tyr Gly Trp Ser Thr Asn Pro Leu Val Glu Tyr Tyr Ile Met Glu
 65                 70                  75                  80

Asp Asn His Asn Tyr Pro Ala Gln Gly Thr Val Lys Gly Thr Val Thr
                85                  90                  95

Ser Asp Gly Ala Thr Tyr Thr Ile Trp Glu Asn Thr Arg Val Asn Glu
            100                 105                 110

Pro Ser Ile Gln Gly Thr Ala Thr Phe Asn Gln Tyr Ile Ser Val Arg
            115                 120                 125

Asn Ser Pro Arg Thr Ser Gly Thr Val Thr Val Gln Asn His Phe Asn
    130                 135                 140

Ala Trp Ala Ser Leu Gly Leu His Leu Gly Gln Met Asn Tyr Gln Val
145                 150                 155                 160

Val Ala Val Glu Gly Trp Gly Gly Ser Gly Ser Ala Ser Gln Ser
                165                 170                 175

Val Ser Asn

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
agctacctcg ccgtgtacgg                                                   20

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
ccaccaagca cggcgaggt                                                    19

<210> SEQ ID NO 5
<211> LENGTH: 33
<212> TYPE: DNA
<213> ORGANISM: Artificial
<220> FEATURE:
<223> OTHER INFORMATION: Primer

<400> SEQUENCE: 5
acgcagcgcg tcaacgcccc gtccatcatc ggc                                    33

<210> SEQ ID NO 6
<211> LENGTH: 33
<212> TYPE: DNA
<213> ORGANISM: Artificial
```

```
<220> FEATURE:
<223> OTHER INFORMATION: Primer

<400> SEQUENCE: 6
aacgccccgt ccatcgaggg caccgccacc ttt                          33

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
ggcaccgcca cctttcgcca gtactggtcc                              30

<210> SEQ ID NO 8
<211> LENGTH: 29
<212> TYPE: DNA
<213> ORGANISM: Artificial
<220> FEATURE:
<223> OTHER INFORMATION: Primer

<400> SEQUENCE: 8
gtccgccgca accgccgctc gagcggctc                               29

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
aaccacttcg acgcgtgg                                           18

<210> SEQ ID NO 10
<211> LENGTH: 33
<212> TYPE: DNA
<213> ORGANISM: Artificial
<220> FEATURE:
<223> OTHER INFORMATION: Primer

<400> SEQUENCE: 10
ttcgacgcgt gggctcgcca cggcctgacg ctc                          33

<210> SEQ ID NO 11
<211> LENGTH: 19
<212> TYPE: DNA
<213> ORGANISM: Artificial
<220> FEATURE:
<223> OTHER INFORMATION: Primer

<400> SEQUENCE: 11
ggctcagcac ggcctgacg                                          19

<210> SEQ ID NO 12
<211> LENGTH: 33
<212> TYPE: DNA
<213> ORGANISM: Artificial
<220> FEATURE:
<223> OTHER INFORMATION: Primer

<400> SEQUENCE: 12
gctcgccacg gcctgcacct cgggacgatg gat                          33
```

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
ggcaacgcca ccttttacca gtactggtcc                                              30

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
ggcaccgcca ccttttacca gtactggtcc                                              30

<210> SEQ ID NO 15
<211> LENGTH: 30
<212> TYPE: DNA
<213> ORGANISM: Artificial
<220> FEATURE:
<223> OTHER INFORMATION: Primer

<400> SEQUENCE: 15
ccctccgtgg aaggcaacaa gaccttccag                                              30

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
gcccacgccg ctagcaccat cacc                                                    24

<210> SEQ ID NO 17
<211> LENGTH: 23
<212> TYPE: DNA
<213> ORGANISM: Artificial
<220> FEATURE:
<223> OTHER INFORMATION: Primer

<400> SEQUENCE: 17
cgtccaccgg taccaggtca acc                                                     23

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
ccatccaggg caacgcgacc ttc                                                     23

<210> SEQ ID NO 19
<211> LENGTH: 24
<212> TYPE: DNA
<213> ORGANISM: Artificial
<220> FEATURE:
<223> OTHER INFORMATION: Primer

```
<400> SEQUENCE: 19
cgtcgtgcta gcatcaacta cgac                                           24

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20
ggatcctagt tgctgacac                                                 19

<210> SEQ ID NO 21
<211> LENGTH: 30
<212> TYPE: DNA
<213> ORGANISM: Artificial
<220> FEATURE:
<223> OTHER INFORMATION: Primer

<400> SEQUENCE: 21
ccgtccatcg agggcaacgc cacctttcgc                                     30

<210> SEQ ID NO 22
<211> LENGTH: 30
<212> TYPE: DNA
<213> ORGANISM: Artificial
<220> FEATURE:
<223> OTHER INFORMATION: Primer

<400> SEQUENCE: 22
gtggagggtt acaacagctc tggctctgct                                     30

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23
gtggagggtt acaacagcac cggctctgct                                     30

<210> SEQ ID NO 24
<211> LENGTH: 30
<212> TYPE: DNA
<213> ORGANISM: Artificial
<220> FEATURE:
<223> OTHER INFORMATION: Primer

<400> SEQUENCE: 24
ggttacttta gcaacggctc tgcttccatc                                     30

<210> SEQ ID NO 25
<211> LENGTH: 30
<212> TYPE: DNA
<213> ORGANISM: Artificial
<220> FEATURE:
<223> OTHER INFORMATION: Primer

<400> SEQUENCE: 25
ggttacttta gcaacggcac cgcttccatc                                     30
```

```
<210> SEQ ID NO 26
<211> LENGTH: 30
<212> TYPE: DNA
<213> ORGANISM: Artificial
<220> FEATURE:
<223> OTHER INFORMATION: Primer

<400> SEQUENCE: 26
ggtcccggcg ggaacttctc cgtcaactgg                                        30

<210> SEQ ID NO 27
<211> LENGTH: 30
<212> TYPE: DNA
<213> ORGANISM: Artificial
<220> FEATURE:
<223> OTHER INFORMATION: Primer

<400> SEQUENCE: 27
ggtcccggcg ggaacttcac cgtcaactgg                                        30

<210> SEQ ID NO 28
<211> LENGTH: 189
<212> TYPE: PRT
<213> ORGANISM: Aspergillus awamori var. kawachi

<400> SEQUENCE: 28

Arg Ser Thr Pro Ser Ser Thr Gly Glu Asn Asn Gly Tyr Tyr Tyr Ser
  1               5                  10                  15

Phe Trp Thr Asp Gly Gly Gly Asp Val Thr Tyr Thr Asn Gly Asn Ala
             20                  25                  30

Gly Ser Tyr Ser Val Glu Trp Ser Asn Val Gly Asn Phe Val Gly Gly
         35                  40                  45

Lys Gly Trp Asn Pro Gly Ser Ala Lys Asp Ile Thr Tyr Ser Gly Asn
     50                  55                  60

Phe Thr Pro Ser Gly Asn Gly Tyr Leu Ser Val Tyr Gly Trp Thr Thr
 65                  70                  75                  80

Asp Pro Leu Ile Glu Tyr Tyr Ile Val Glu Ser Tyr Gly Asp Tyr Asn
                 85                  90                  95

Pro Gly Ser Gly Gly Thr Thr Arg Gly Asn Val Ser Ser Asp Gly Ser
            100                 105                 110

Val Tyr Asp Ile Tyr Thr Ala Thr Arg Thr Asn Ala Pro Ser Ile Gln
        115                 120                 125

Gly Thr Ala Thr Phe Ser Gln Tyr Trp Ser Val Arg Gln Asn Lys Arg
    130                 135                 140

Val Gly Gly Thr Val Thr Thr Ser Asn His Phe Asn Ala Trp Ala Lys
145                 150                 155                 160

Leu Gly Met Asn Leu Gly Thr His Asn Tyr Gln Ile Leu Ala Thr Glu
                165                 170                 175

Gly Tyr Gln Ser Ser Gly Ser Ser Ile Thr Ile Gln
            180                 185

<210> SEQ ID NO 29
<211> LENGTH: 184
<212> TYPE: PRT
<213> ORGANISM: Aspergillus tubingensis
```

<400> SEQUENCE: 29

```
Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Thr Tyr Ser Ala Glu Tyr Ser Ala Ser Gly Ser Ala
    50                  55                  60

Ser Tyr Leu Ala Val Tyr Gly Trp Val Asn Tyr Pro Gln Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala His His Gly Phe Gly Asn Ser
145                 150                 155                 160

Asp Phe Asn Tyr Gln Val Val Ala Val Glu Ala Trp Ser Gly Ala Gly
                165                 170                 175

Ser Ala Ser Val Thr Ile Ser Ser
            180
```

<210> SEQ ID NO 30
<211> LENGTH: 185
<212> TYPE: PRT
<213> ORGANISM: Bacillus circulans

<400> SEQUENCE: 30

```
Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Thr Asn His Val Asn Ala Trp Lys Ser His Gly Met Asn Leu
145                 150                 155                 160
```

```
Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 31
<211> LENGTH: 201
<212> TYPE: PRT
<213> ORGANISM: Bacillus pumilus

<400> SEQUENCE: 31

Arg Thr Ile Thr Asn Asn Glu Met Gly Asn His Ser Gly Tyr Asp Tyr
1               5                   10                  15

Glu Leu Trp Lys Asp Tyr Gly Asn Thr Ser Met Thr Leu Asn Asn Gly
            20                  25                  30

Gly Ala Phe Ser Ala Gly Trp Asn Asn Ile Gly Asn Ala Leu Phe Arg
        35                  40                  45

Lys Gly Lys Lys Phe Asp Ser Thr Arg Thr His His Gln Leu Gly Asn
    50                  55                  60

Ile Ser Ile Asn Tyr Asn Ala Ser Phe Asn Pro Gly Gly Asn Ser Tyr
65                  70                  75                  80

Leu Cys Val Tyr Gly Trp Thr Gln Ser Pro Leu Ala Glu Tyr Tyr Ile
                85                  90                  95

Val Asp Ser Trp Gly Thr Tyr Arg Pro Thr Gly Ala Tyr Lys Gly Ser
            100                 105                 110

Phe Tyr Ala Asp Gly Gly Thr Tyr Asp Ile Tyr Glu Thr Thr Arg Val
        115                 120                 125

Asn Gln Pro Ser Ile Ile Gly Ile Ala Thr Phe Lys Gln Tyr Trp Ser
    130                 135                 140

Val Arg Gln Thr Lys Arg Thr Ser Gly Thr Val Ser Val Ser Ala His
145                 150                 155                 160

Phe Arg Lys Trp Glu Ser Leu Gly Met Pro Met Gly Lys Met Tyr Glu
                165                 170                 175

Thr Ala Phe Thr Val Glu Gly Tyr Gln Ser Ser Gly Ser Ala Asn Val
            180                 185                 190

Met Thr Asn Gln Leu Phe Ile Gly Asn
        195                 200

<210> SEQ ID NO 32
<211> LENGTH: 185
<212> TYPE: PRT
<213> ORGANISM: Bacillus subtilus

<400> SEQUENCE: 32

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95
```

```
Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 33
<211> LENGTH: 211
<212> TYPE: PRT
<213> ORGANISM: Clostridium acetobutylicum

<400> SEQUENCE: 33

Ser Ala Phe Asn Thr Gln Ala Ala Pro Lys Thr Ile Thr Ser Asn Glu
1               5                   10                  15

Ile Gly Val Asn Gly Gly Tyr Asp Tyr Glu Leu Trp Lys Asp Tyr Gly
            20                  25                  30

Asn Thr Ser Met Thr Leu Lys Asn Gly Gly Ala Phe Ser Cys Gln Trp
        35                  40                  45

Ser Asn Ile Gly Asn Ala Leu Phe Arg Lys Gly Lys Lys Phe Asn Asp
50                  55                  60

Thr Gln Thr Tyr Lys Gln Leu Gly Asn Ile Ser Val Asn Tyr Asn Cys
65                  70                  75                  80

Asn Tyr Gln Pro Tyr Gly Asn Ser Tyr Leu Cys Val Tyr Gly Trp Thr
                85                  90                  95

Ser Ser Pro Leu Val Glu Tyr Tyr Ile Val Asp Ser Trp Gly Ser Trp
            100                 105                 110

Arg Pro Pro Gly Gly Thr Ser Lys Gly Thr Ile Thr Val Asp Gly Gly
            115                 120                 125

Ile Tyr Asp Ile Tyr Glu Thr Thr Arg Ile Asn Gln Pro Ser Ile Gln
130                 135                 140

Gly Asn Thr Thr Phe Lys Gln Tyr Trp Ser Val Arg Arg Thr Lys Arg
145                 150                 155                 160

Thr Ser Gly Thr Ile Ser Val Ser Lys His Phe Ala Ala Trp Glu Ser
                165                 170                 175

Lys Gly Met Pro Leu Gly Lys Met His Glu Thr Ala Phe Asn Ile Glu
            180                 185                 190

Gly Tyr Gln Ser Ser Gly Lys Ala Asp Val Asn Ser Met Ser Ile Asn
            195                 200                 205

Ile Gly Lys
    210

<210> SEQ ID NO 34
<211> LENGTH: 206
<212> TYPE: PRT
<213> ORGANISM: Clostridium stercorarium
```

```
<400> SEQUENCE: 34

Gly Arg Ile Ile Tyr Asp Asn Glu Thr Gly Thr His Gly Gly Tyr Asp
1               5                   10                  15

Tyr Glu Leu Trp Lys Asp Tyr Gly Asn Thr Ile Met Glu Leu Asn Asp
                20                  25                  30

Gly Gly Thr Phe Ser Cys Gln Trp Ser Asn Ile Gly Asn Ala Leu Phe
            35                  40                  45

Arg Lys Gly Arg Lys Phe Asn Ser Asp Lys Thr Tyr Gln Glu Leu Gly
        50                  55                  60

Asp Ile Val Val Glu Tyr Gly Cys Asp Tyr Asn Pro Asn Gly Asn Ser
65                  70                  75                  80

Tyr Leu Cys Val Tyr Gly Trp Thr Arg Asn Pro Leu Val Glu Tyr Tyr
                85                  90                  95

Ile Val Glu Ser Trp Gly Ser Trp Arg Pro Pro Gly Ala Thr Pro Lys
                100                 105                 110

Gly Thr Ile Thr Gln Trp Met Ala Gly Thr Tyr Glu Ile Tyr Glu Thr
            115                 120                 125

Thr Arg Val Asn Gln Pro Ser Ile Asp Gly Thr Ala Thr Phe Gln Gln
        130                 135                 140

Tyr Trp Ser Val Arg Thr Ser Lys Arg Thr Ser Gly Thr Ile Ser Val
145                 150                 155                 160

Thr Glu His Phe Lys Gln Trp Glu Arg Met Gly Met Arg Met Gly Lys
                165                 170                 175

Met Tyr Glu Val Ala Leu Thr Val Glu Gly Tyr Gln Ser Ser Gly Tyr
                180                 185                 190

Ala Asn Val Tyr Lys Asn Glu Ile Arg Ile Gly Ala Asn Pro
            195                 200                 205

<210> SEQ ID NO 35
<211> LENGTH: 211
<212> TYPE: PRT
<213> ORGANISM: Ruminococcus flavefaciens

<400> SEQUENCE: 35

Ser Ala Ala Asp Gln Gln Thr Arg Gly Asn Val Gly Gly Tyr Asp Tyr
1               5                   10                  15

Glu Met Trp Asn Gln Asn Gly Gln Gly Gln Ala Ser Met Asn Pro Gly
                20                  25                  30

Ala Gly Ser Phe Thr Cys Ser Trp Ser Asn Ile Glu Asn Phe Leu Ala
            35                  40                  45

Arg Met Gly Lys Asn Tyr Asp Ser Gln Lys Lys Asn Tyr Lys Ala Phe
        50                  55                  60

Gly Asn Ile Val Leu Thr Tyr Asp Val Glu Tyr Thr Pro Arg Gly Asn
65                  70                  75                  80

Ser Tyr Met Cys Val Tyr Gly Trp Thr Arg Asn Pro Leu Met Glu Tyr
                85                  90                  95

Tyr Ile Val Glu Gly Trp Gly Asp Trp Arg Pro Pro Gly Asn Asp Gly
                100                 105                 110

Glu Val Lys Gly Thr Val Ser Ala Asn Gly Asn Thr Tyr Asp Ile Arg
            115                 120                 125

Lys Thr Met Arg Tyr Asn Gln Pro Ser Leu Asp Gly Thr Ala Thr Phe
        130                 135                 140

Pro Gln Tyr Trp Ser Val Arg Gln Thr Ser Gly Ser Ala Asn Asn Gln
145                 150                 155                 160
```

```
Thr Asn Tyr Met Lys Gly Thr Ile Asp Val Thr Lys His Phe Asp Ala
                165                 170                 175

Trp Ser Ala Ala Gly Leu Asp Met Ser Gly Thr Leu Tyr Glu Val Ser
            180                 185                 190

Leu Asn Ile Glu Gly Tyr Arg Ser Asn Gly Ser Ala Asn Val Lys Ser
        195                 200                 205

Val Ser Val
    210

<210> SEQ ID NO 36
<211> LENGTH: 197
<212> TYPE: PRT
<213> ORGANISM: Schizophyllum commune

<400> SEQUENCE: 36

Ser Gly Thr Pro Ser Ser Thr Gly Thr Asp Gly Gly Tyr Tyr Tyr Ser
1               5                   10                  15

Trp Trp Thr Asp Gly Ala Gly Asp Ala Thr Tyr Gln Asn Asn Gly Gly
            20                  25                  30

Gly Ser Tyr Thr Leu Thr Trp Ser Gly Asn Asn Gly Asn Leu Val Gly
        35                  40                  45

Gly Lys Gly Trp Asn Pro Gly Ala Ala Ser Arg Ser Ile Ser Tyr Ser
    50                  55                  60

Gly Thr Tyr Gln Pro Asn Gly Asn Ser Tyr Leu Ser Val Tyr Gly Trp
65                  70                  75                  80

Thr Arg Ser Ser Leu Ile Glu Tyr Tyr Ile Val Glu Ser Tyr Gly Ser
                85                  90                  95

Tyr Asp Pro Ser Ser Ala Ala Ser His Lys Gly Ser Val Thr Cys Asn
            100                 105                 110

Gly Ala Thr Tyr Asp Ile Leu Ser Thr Trp Arg Tyr Asn Ala Pro Ser
        115                 120                 125

Ile Asp Gly Thr Gln Thr Phe Glu Gln Phe Trp Ser Val Arg Asn Pro
    130                 135                 140

Lys Lys Ala Pro Gly Gly Ser Ile Ser Gly Thr Val Asp Val Gln Cys
145                 150                 155                 160

His Phe Asp Ala Trp Lys Gly Leu Gly Met Asn Leu Gly Ser Glu His
                165                 170                 175

Asn Tyr Gln Ile Val Ala Thr Glu Gly Tyr Gln Ser Ser Gly Thr Ala
            180                 185                 190

Thr Ile Thr Val Thr
        195

<210> SEQ ID NO 37
<211> LENGTH: 189
<212> TYPE: PRT
<213> ORGANISM: Streptomyces sp.

<400> SEQUENCE: 37

Ala Thr Thr Ile Thr Asn Glu Thr Gly Tyr Asp Gly Met Tyr Tyr Ser
1               5                   10                  15

Phe Trp Thr Asp Gly Gly Ser Val Ser Met Thr Leu Asn Gly Gly Gly
            20                  25                  30

Gly Ser Tyr Ser Thr Arg Trp Thr Asn Cys Gly Asn Phe Val Ala Gly
        35                  40                  45

Lys Gly Trp Ala Asn Gly Gly Arg Arg Thr Val Arg Tyr Thr Gly Trp
    50                  55                  60
```

-continued

```
Phe Asn Pro Ser Gly Asn Gly Tyr Gly Cys Leu Tyr Gly Trp Thr Ser
 65                  70                  75                  80

Asn Pro Leu Val Glu Tyr Tyr Ile Val Asp Asn Trp Gly Ser Tyr Arg
                 85                  90                  95

Pro Thr Gly Glu Thr Arg Gly Thr Val His Ser Asp Gly Gly Thr Tyr
            100                 105                 110

Asp Ile Tyr Lys Thr Thr Arg Tyr Asn Ala Pro Ser Val Glu Ala Pro
        115                 120                 125

Ala Ala Phe Asp Gln Tyr Trp Ser Val Arg Gln Ser Lys Val Thr Ser
    130                 135                 140

Gly Thr Ile Thr Thr Gly Asn His Phe Asp Ala Trp Ala Arg Ala Gly
145                 150                 155                 160

Met Asn Met Gly Asn Phe Arg Tyr Tyr Met Ile Asn Ala Thr Glu Gly
                165                 170                 175

Tyr Gln Ser Ser Gly Ser Ser Thr Ile Thr Val Ser Gly
            180                 185

<210> SEQ ID NO 38
<211> LENGTH: 191
<212> TYPE: PRT
<213> ORGANISM: Streptomyces lividans

<400> SEQUENCE: 38

Asp Thr Val Val Thr Thr Asn Gln Glu Gly Thr Asn Asn Gly Tyr Tyr
 1               5                  10                  15

Tyr Ser Phe Trp Thr Asp Ser Gln Gly Thr Val Ser Met Asn Met Gly
                 20                  25                  30

Ser Gly Gly Gln Tyr Ser Thr Ser Trp Arg Asn Thr Gly Asn Phe Val
             35                  40                  45

Ala Gly Lys Gly Trp Ala Asn Gly Gly Arg Arg Thr Val Gln Tyr Ser
    50                  55                  60

Gly Ser Phe Asn Pro Ser Gly Asn Ala Tyr Leu Ala Leu Tyr Gly Trp
 65                  70                  75                  80

Thr Ser Asn Pro Leu Val Glu Tyr Tyr Ile Val Asp Asn Trp Gly Thr
                 85                  90                  95

Tyr Arg Pro Thr Gly Glu Tyr Lys Gly Thr Val Thr Ser Asp Gly Gly
            100                 105                 110

Thr Tyr Asp Ile Tyr Lys Thr Thr Arg Val Asn Lys Pro Ser Val Glu
        115                 120                 125

Gly Thr Arg Thr Phe Asp Gln Tyr Trp Ser Val Arg Gln Ser Lys Arg
    130                 135                 140

Thr Gly Gly Thr Ile Thr Thr Gly Asn His Phe Asp Ala Trp Ala Arg
145                 150                 155                 160

Ala Gly Met Pro Leu Gly Asn Phe Ser Tyr Tyr Met Ile Met Ala Thr
                165                 170                 175

Glu Gly Tyr Gln Ser Ser Gly Ser Ser Ser Ile Asn Val Gly Gly
            180                 185                 190

<210> SEQ ID NO 39
<211> LENGTH: 191
<212> TYPE: PRT
<213> ORGANISM: Streptomyces lividans
```

```
<400> SEQUENCE: 39

Ala Thr Thr Ile Thr Thr Asn Gln Thr Gly Thr Asp Gly Met Tyr Tyr
1               5                   10                  15

Ser Phe Trp Thr Asp Gly Gly Ser Val Ser Met Thr Leu Asn Gly
            20                  25                  30

Gly Gly Ser Tyr Ser Thr Gln Trp Thr Asn Cys Gly Asn Phe Val Ala
        35                  40                  45

Gly Lys Gly Trp Ser Thr Gly Asp Gly Asn Val Arg Tyr Asn Gly Tyr
50                  55                  60

Phe Asn Pro Val Gly Asn Gly Tyr Gly Cys Leu Tyr Gly Trp Thr Ser
65                  70                  75                  80

Asn Pro Leu Val Glu Tyr Tyr Ile Val Asp Asn Trp Gly Ser Tyr Arg
                85                  90                  95

Pro Thr Gly Thr Tyr Lys Gly Thr Val Ser Ser Asp Gly Gly Thr Tyr
            100                 105                 110

Asp Ile Tyr Gln Thr Thr Arg Tyr Asn Ala Pro Ser Val Glu Gly Thr
        115                 120                 125

Lys Thr Phe Gln Gln Tyr Trp Ser Val Arg Gln Ser Lys Val Thr Ser
130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Met Ala Thr
                165                 170                 175

Glu Gly Tyr Gln Ser Ser Gly Ser Ser Asn Ile Thr Val Ser Gly
            180                 185                 190

<210> SEQ ID NO 40
<211> LENGTH: 189
<212> TYPE: PRT
<213> ORGANISM: Thermomonospora fusca

<400> SEQUENCE: 40

Ala Val Thr Ser Asn Glu Thr Gly Tyr His Asp Gly Tyr Phe Tyr Ser
1               5                   10                  15

Phe Trp Thr Asp Ala Pro Gly Thr Val Ser Met Glu Leu Gly Pro Gly
            20                  25                  30

Gly Asn Tyr Ser Thr Ser Trp Arg Asn Thr Gly Asn Phe Val Ala Gly
        35                  40                  45

Lys Gly Trp Ala Thr Gly Gly Arg Arg Thr Val Thr Tyr Ser Ala Ser
50                  55                  60

Phe Asn Pro Ser Gly Asn Ala Tyr Leu Thr Leu Tyr Gly Trp Thr Arg
65                  70                  75                  80

Asn Pro Leu Val Glu Tyr Tyr Ile Val Glu Ser Trp Gly Thr Tyr Arg
                85                  90                  95

Pro Thr Gly Thr Tyr Met Gly Thr Val Thr Thr Asp Gly Gly Thr Tyr
            100                 105                 110

Asp Ile Tyr Lys Thr Thr Arg Tyr Asn Ala Pro Ser Ile Glu Gly Thr
        115                 120                 125

Arg Thr Phe Asp Gln Tyr Trp Ser Val Arg Gln Ser Lys Arg Thr Ser
130                 135                 140

Gly Thr Ile Thr Ala Gly Asn His Phe Asp Ala Trp Ala Arg His Gly
145                 150                 155                 160
```

Met His Leu Gly Thr His Asp Tyr Met Ile Met Ala Thr Glu Gly Tyr
            165                 170                 175

Gln Ser Ser Gly Ser Ser Asn Val Thr Leu Gly Thr Ser
            180                 185

<210> SEQ ID NO 41
<211> LENGTH: 190
<212> TYPE: PRT
<213> ORGANISM: Trichoderma harzianum

<400> SEQUENCE: 41

Gln Thr Ile Gly Pro Gly Thr Gly Tyr Ser Asn Gly Tyr Tyr Tyr Ser
1               5                   10                  15

Tyr Trp Asn Asp Gly His Ala Gly Val Thr Tyr Thr Asn Gly Gly Gly
            20                  25                  30

Gly Ser Phe Thr Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
50                  55                  60

Ser Tyr Asn Pro Asn Gly Asn Ser Tyr Leu Ser Ile Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 42
<211> LENGTH: 190
<212> TYPE: PRT
<213> ORGANISM: Trichoderma viride

<400> SEQUENCE: 42

Gln Thr Ile Gly Pro Gly Thr Gly Phe Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
50                  55                  60

Thr Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

```
Ser Val Tyr Asp Ile Tyr Arg Thr Gln Arg Val Asn Gln Pro Ser Ile
        115                 120                 125

Ile Gly Thr Ser Thr Phe Tyr Gln Tyr Trp Ser Val Arg Arg Thr His
130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190
```

<210> SEQ ID NO 43
<211> LENGTH: 184
<212> TYPE: PRT
<213> ORGANISM: Aspergillus niger

<400> SEQUENCE: 43

```
Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Thr Tyr Ser Ala Glu Tyr Ser Ala Ser Gly Ser Ser
    50                  55                  60

Ser Tyr Leu Ala Val Tyr Gly Trp Val Asn Tyr Pro Gly Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Ile Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
130                 135                 140

Val Ala Asn His Phe Asn Phe Trp Ala Gln His Gly Phe Gly Asn Ser
145                 150                 155                 160

Asp Phe Asn Tyr Gln Val Met Ala Val Glu Ala Trp Ser Gly Ala Gly
                165                 170                 175

Ser Ala Ser Val Thr Ile Ser Ser
            180
```

<210> SEQ ID NO 44
<211> LENGTH: 184
<212> TYPE: PRT
<213> ORGANISM: Aspergillus kawachii

<400> SEQUENCE: 44

```
Ser Ala Gly Ile Asn Tyr Val Gln Asn Tyr Asn Gly Asn Leu Ala Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Ser Tyr Ser Ala Glu Tyr Ser Ala Ser Gly Ser Ser
    50                  55                  60
```

```
Ser Tyr Leu Ala Val Tyr Gly Trp Val Asn Tyr Pro Gln Ala Glu Tyr
 65                  70                  75                  80

Tyr Ile Val Glu Asp Tyr Gly Asp Tyr Asn Pro Cys Ser Ser Ala Thr
                 85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
        130                 135                 140

Val Ala Asn His Phe Asn Phe Trp Ala Gln His Gly Phe Gly Asn Ser
145                 150                 155                 160

Asp Phe Asn Tyr Gln Val Met Ala Val Glu Ala Trp Ser Gly Ala Gly
                165                 170                 175

Ser Ala Ser Val Thr Ile Ser Ser
            180

<210> SEQ ID NO 45
<211> LENGTH: 202
<212> TYPE: PRT
<213> ORGANISM: Fibrobacter succinogenes

<400> SEQUENCE: 45

Asn Ser Ser Val Thr Gly Asn Val Gly Ser Ser Pro Tyr His Tyr Glu
 1               5                  10                  15

Ile Trp Tyr Gln Gly Gly Asn Asn Ser Met Thr Phe Tyr Asp Asn Gly
                20                  25                  30

Thr Tyr Lys Ala Ser Trp Asn Gly Thr Asn Asp Phe Leu Ala Arg Val
            35                  40                  45

Gly Phe Lys Tyr Asp Glu Lys His Thr Tyr Glu Glu Leu Gly Pro Ile
        50                  55                  60

Asp Ala Tyr Tyr Lys Trp Ser Lys Gln Gly Ser Ala Gly Gly Tyr Asn
 65                  70                  75                  80

Tyr Ile Gly Ile Tyr Gly Trp Thr Val Asp Pro Leu Val Glu Tyr Tyr
                 85                  90                  95

Ile Val Asp Asp Trp Phe Asn Lys Pro Gly Ala Asn Leu Leu Gly Gln
            100                 105                 110

Arg Lys Gly Glu Phe Thr Val Asp Gly Asp Thr Tyr Glu Ile Trp Gln
        115                 120                 125

Asn Thr Arg Val Gln Gln Pro Ser Ile Lys Gly Thr Gln Thr Phe Pro
130                 135                 140

Gln Tyr Phe Ser Val Arg Lys Ser Ala Arg Ser Cys Gly His Ile Asp
145                 150                 155                 160

Ile Thr Ala His Met Lys Lys Trp Glu Glu Leu Gly Met Lys Met Gly
                165                 170                 175

Lys Met Tyr Glu Ala Lys Val Leu Val Glu Ala Gly Gly Ser Gly
            180                 185                 190

Ser Phe Asp Val Thr Tyr Phe Lys Met Thr
        195                 200

<210> SEQ ID NO 46
<211> LENGTH: 194
<212> TYPE: PRT
<213> ORGANISM: Thermomyces lanuginosus
```

<400> SEQUENCE: 46

```
Gln Thr Thr Pro Asn Ser Glu Gly Trp His Asp Gly Tyr Tyr Tyr Ser
1               5                   10                  15

Trp Trp Ser Asp Gly Gly Ala Gln Ala Thr Tyr Thr Asn Leu Glu Gly
            20                  25                  30

Gly Thr Tyr Glu Ile Ser Trp Gly Asp Gly Gly Asn Leu Val Gly Gly
        35                  40                  45

Lys Gly Trp Asn Pro Gly Leu Asn Ala Arg Ala Ile His Phe Glu Gly
    50                  55                  60

Val Tyr Gln Pro Asn Gly Asn Ser Tyr Leu Ala Val Tyr Gly Trp Thr
65                  70                  75                  80

Arg Asn Pro Leu Val Glu Tyr Tyr Ile Val Glu Asn Phe Gly Thr Tyr
                85                  90                  95

Asp Pro Ser Ser Gly Ala Thr Asp Leu Gly Thr Val Glu Cys Asp Gly
            100                 105                 110

Ser Ile Tyr Arg Leu Gly Lys Thr Thr Arg Val Asn Ala Pro Ser Ile
        115                 120                 125

Asp Gly Thr Gln Thr Phe Asp Gln Tyr Trp Ser Val Arg Gln Asp Lys
    130                 135                 140

Arg Thr Ser Gly Thr Val Gln Thr Gly Cys His Phe Asp Ala Trp Ala
145                 150                 155                 160

Arg Ala Gly Leu Asn Val Asn Gly Asp His Tyr Tyr Gln Ile Val Ala
                165                 170                 175

Thr Glu Gly Tyr Phe Ser Ser Gly Tyr Ala Arg Ile Thr Val Ala Asp
            180                 185                 190

Val Gly
```

<210> SEQ ID NO 47
<211> LENGTH: 178
<212> TYPE: PRT
<213> ORGANISM: T. reesei

<400> SEQUENCE: 47

```
Ala Ser Ile Asn Tyr Asp Gln Asn Tyr Gln Thr Gly Gly Gln Val Ser
1               5                   10                  15

Tyr Ser Pro Ser Asn Thr Gly Phe Ser Val Asn Trp Asn Thr Gln Asp
            20                  25                  30

Asp Phe Val Val Gly Val Gly Trp Thr Thr Gly Ser Ser Ala Pro Ile
        35                  40                  45

Asn Phe Gly Gly Ser Phe Ser Val Asn Ser Gly Thr Gly Leu Leu Ser
    50                  55                  60

Val Tyr Gly Trp Ser Thr Asn Pro Leu Val Glu Tyr Tyr Ile Met Glu
65                  70                  75                  80

Asp Asn His Asn Tyr Pro Ala Gln Gly Thr Val Lys Gly Thr Val Thr
                85                  90                  95

Ser Asp Gly Ala Thr Tyr Thr Ile Trp Glu Asn Thr Arg Val Asn Glu
            100                 105                 110

Pro Ser Ile Gln Gly Asn Ala Thr Phe Asn Gln Tyr Ile Ser Val Arg
        115                 120                 125

Asn Ser Pro Arg Thr Ser Gly Thr Val Thr Val Gln Asn His Phe Asn
    130                 135                 140

Trp Ala Ser Leu Gly Leu His Leu Gly Gln Met Met Asn Tyr Gln Val
145                 150                 155                 160
```

-continued

```
Val Ala Val Glu Gly Trp Gly Ser Gly Ser Ala Ser Gln Ser Val
                165                 170                 175

Ser Asn

<210> SEQ ID NO 48
<211> LENGTH: 191
<212> TYPE: PRT
<213> ORGANISM: Streptomyces lividans

<400> SEQUENCE: 48

Ala Thr Thr Ile Thr Thr Asn Gln Thr Gly Thr Asp Gly Met Tyr Tyr
1               5                   10                  15

Ser Phe Trp Thr Asp Gly Gly Gly Ser Val Ser Met Thr Leu Asn Gly
                20                  25                  30

Gly Gly Ser Tyr Ser Thr Gln Trp Thr Asn Cys Gly Asn Phe Val Ala
            35                  40                  45

Gly Lys Gly Trp Ser Thr Gly Asp Gly Asn Val Arg Tyr Asn Gly Tyr
        50                  55                  60

Phe Asn Pro Val Gly Asn Gly Tyr Gly Cys Leu Tyr Gly Trp Thr Ser
65                  70                  75                  80

Asn Pro Leu Val Glu Tyr Tyr Ile Val Asp Asn Trp Gly Ser Tyr Arg
                85                  90                  95

Pro Thr Gly Thr Tyr Lys Gly Thr Val Ser Ser Asp Gly Gly Thr Tyr
                100                 105                 110

Asp Ile Tyr Gln Thr Thr Arg Tyr Asn Ala Pro Ser Val Glu Gly Asn
            115                 120                 125

Lys Thr Phe Gln Gln Tyr Trp Ser Val Arg Gln Ser Lys Val Thr Ser
        130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Met Ala Thr
                165                 170                 175

Glu Gly Tyr Gln Ser Ser Gly Ser Ser Asn Ile Thr Val Ser Gly
                180                 185                 190
```